(12) United States Patent
Clegg et al.

(10) Patent No.: US 10,111,948 B2
(45) Date of Patent: Oct. 30, 2018

(54) SYNTHETIC HAPTEN CARRIER COMPOSITIONS AND METHODS

(71) Applicant: TRIA BIOSCIENCE CORP., Seattle, WA (US)

(72) Inventors: Christopher H. Clegg, Seattle, WA (US); Keith D. Miller, Moscow, ID (US)

(73) Assignee: TRIA BIOSCIENCE CORP., Seattle, WA (US)

( * ) Notice: Subject to any disclaimer, the term of this patent is extended or adjusted under 35 U.S.C. 154(b) by 0 days.

(21) Appl. No.: 15/306,466

(22) PCT Filed: Apr. 24, 2015

(86) PCT No.: PCT/US2015/027612
§ 371 (c)(1),
(2) Date: Oct. 24, 2016

(87) PCT Pub. No.: WO2015/164798
PCT Pub. Date: Oct. 29, 2015

(65) Prior Publication Data
US 2017/0049883 A1    Feb. 23, 2017

Related U.S. Application Data

(60) Provisional application No. 61/984,629, filed on Apr. 25, 2014.

(51) Int. Cl.
| A61K 39/385 | (2006.01) |
| A61K 38/00 | (2006.01) |
| C07K 14/005 | (2006.01) |
| C07K 14/725 | (2006.01) |
| A61K 39/00 | (2006.01) |

(52) U.S. Cl.
CPC ............ *A61K 39/385* (2013.01); *A61K 38/00* (2013.01); *A61K 39/0013* (2013.01); *C07K 14/005* (2013.01); *C07K 14/7051* (2013.01); *A61K 2039/55505* (2013.01); *A61K 2039/55566* (2013.01); *A61K 2039/575* (2013.01); *A61K 2039/6031* (2013.01); *C07K 2319/00* (2013.01); *C07K 2319/73* (2013.01); *C12N 2760/16122* (2013.01); *C12N 2760/16134* (2013.01); *C12N 2760/16141* (2013.01)

(58) Field of Classification Search
None
See application file for complete search history.

(56) References Cited

U.S. PATENT DOCUMENTS

| 4,321,387 A | 3/1982 | Chavdarian et al. |
| 4,442,292 A | 4/1984 | Edwards, III |
| 4,965,074 A | 10/1990 | Leeson |
| 4,966,916 A | 10/1990 | Abood |
| 5,057,540 A | 10/1991 | Kensil et al. |
| 5,069,094 A | 12/1991 | Birkestrand |
| 5,138,062 A | 8/1992 | Osdene et al. |
| 5,214,060 A | 5/1993 | Caldwell et al. |
| 5,223,497 A | 6/1993 | Gawin et al. |
| 5,227,391 A | 7/1993 | Caldwell et al. |
| 5,232,933 A | 8/1993 | Lippiello et al. |
| 5,242,934 A | 9/1993 | Lippiello et al. |
| 5,276,043 A | 1/1994 | Lippiello et al. |
| 5,278,045 A | 1/1994 | Tam |
| 5,278,176 A | 1/1994 | Lin |
| 5,721,257 A | 2/1998 | Baker et al. |
| 5,736,142 A | 4/1998 | Sette et al. |
| 5,776,957 A | 7/1998 | Crooks et al. |
| 6,413,935 B1 | 7/2002 | Sette et al. |
| 7,402,572 B2 | 7/2008 | Krieg et al. |
| 8,609,114 B2 | 12/2013 | Reed et al. |
| 2009/0183270 A1* | 7/2009 | Adams ............... C07K 14/4702 800/260 |
| 2010/0015173 A1* | 1/2010 | Boato ................. A61K 39/015 424/193.1 |
| 2012/0015000 A1 | 1/2012 | Lanar et al. |
| 2013/0333061 A1* | 12/2013 | Wu ...................... C07K 14/415 800/260 |

FOREIGN PATENT DOCUMENTS

| CA | 228822 A | 2/1923 |
| EP | 0772619 A1 | 5/1997 |
| GB | 2220211 A | 1/1990 |
| WO | WO-2006130328 A2 | 12/2006 |
| WO | WO-2008068017 A1 | 6/2008 |
| WO | WO-2009109428 A2 | 9/2009 |
| WO | WO-2009149252 A1 | 12/2009 |
| WO | WO-2009155789 A1 | 12/2009 |
| WO | WO-2010002818 A2 | 1/2010 |
| WO | WO-2014090905 A1 | 6/2014 |
| WO | WO-2015164798 A1 | 10/2015 |

OTHER PUBLICATIONS

Alexander et al., Development of high potency universal DR-restricted helper epitopes by modification of high affinity DR-blocking peptides. Immunity 1.9 (1994): 751-761.

Altschul, et al. Basic local alignment search tool. Journal of Molecular Biology 215.3 (1990): 403-410.

(Continued)

*Primary Examiner* — Adam Weidner
(74) *Attorney, Agent, or Firm* — Wilson Sonsini Goodrich & Rosati

(57) ABSTRACT

The present disclosure relates to peptide monomers comprising an amphipathic ?-helical peptide, and optionally, at least one T cell epitope peptide; and to dimers and trimers comprising the peptide monomers. The monomeric, dimeric, and trimeric peptides may be conjugated to at least one hapten, wherein the hapten is linked to a lysine or aspartic acid residue of the peptide monomer. These peptide conjugates are useful as vaccine delivery vehicles.

36 Claims, 15 Drawing Sheets

Specification includes a Sequence Listing.

(56) References Cited

OTHER PUBLICATIONS

Altschul et al., Iterated profile searches with PSI-BLAST—a tool for discovery in protein databases. Trends in Biochemical Sciences 23.11 (1998).

Aranda, Fernando, et al., Trial Watch: Peptide vaccines in cancer therapy. OncoImmunology 2 (2013): 10.4161/onci.26621.

Bernstein et al., Effect of imiquimod as an adjuvant for immunotherapy of genital HSV in guinea-pigs. Vaccine 13 (1995): 72-6.

Bhasin et al., MHCBN: a comprehensive database of MHC binding and non-binding peptides. Bioinformatics 19 (2003): 665-6.

Bian et al. Discovery of promiscuous HLA-II-restricted T cell epitopes with TEPITOPE. Method 34 (2004): 468-475.

Biniossek et al., Proteomic identification of protease cleavage sites characterizes prime and non-prime specificity of cysteine cathepsins B, L, and S. J. Proteome Res. 10 (2011): 5363-73.

Brusic et al., Prediction of promiscuous peptides that bind HLA class I molecules. Immunology & Cell Biology 80 (2002): 280-5.

Burkhard et al., Design of a minimal protein oligomerization domain by a structural approach. Protein Sci. 9 (2000): 2294-301.

Burkhard et al., Improving coiled-coil stability by optimizing ionic interactions. J. Mol. Biol. 318 (2002): 901-10.

Burkhard, P. et al. Coiled coils: a highly versatile protein folding motif, Trends in Cell Biology, 11.2 (Feb. 2001): 82-88.

Carter et al., Role of Adjuvants in Modeling the Immune Response. Current Opinion HIV and AIDS 5 (2010): 409-13.

Clegg et al. Adjuvant solution for pandemic influenza vaccine production. Proc. Natl. Acad. Sci. USA 109 (2012): 17585-90.

Coler et al., A synthetic adjuvant to enhance and expand immune responses to influenza vaccines. PLoS One. 5.10 (2010): e13677.

Dalziel et al., Emerging Principles for the Therapeutic Exploitation of Glycosylation. Science 343.1235681 (2014): DOI: 10.1126/science.1235681.

De Rosa, Vaccine applications of flow cytometry, Methods 57 ( 2012): 383-91.

De Villiers, et al., Increased efficacy of a trivalent nicotine vaccine compared to a doese-matched monovalent vaccine when formulated with alum. Vaccine 31 (2013): 6185-6193.

De Villiers et al., Nicotine hapten structure, antibody selectivity and effect relationships: Results from a nicotine vaccine screening procedure. Vaccine 28 (2010): 2161-8.

Dick et al., Conjugate Vaccines. Contribu. Microl. Immunol. Karger, Basel 10 (1989): 48-114.

Didierlaurent et al. AS04, an aluminum salt- and TLR4 agonist-based adjuvant system, induces a transient localized innate immune response leading to enhanced adaptive immunity. J Immunol 183 (2009): 6186-6197.

European search report with written opinion dated Mar. 15, 2017 for EP Application No. 15783769.

Fiore, MC, et al., Treating Tobacco Use and Dependence, Quick Reference Guide for Clinicians. surgeongeneral.gov/tobacco/tobaqrg.htm (2000).

Frank et al., Simultaneous multiple peptide synthesis under continuous flow conditions on cellulose paper discs as segmental solid supports. Tetrahedron 44 (1988): 6031-6040.

Fraser et al., Generation of a universal CD4 memory T cell recall peptide effective in humans, mice and non-human primates. Vaccine 32 (2014): 2896-903.

Friguet et al., Measurements of the true affinity constant in solution of antigen-antibody complexes by enzyme-linked immunosorbent assay. Journal of Immunological Methods 77 (1985): 305-19.

G3H669, UniProtKB/TrEMBL Accession No. G3H669, May 1, 2013 [Online].

Gasteiger et al., ExPASy: the proteomics server for in-depth protein knowledge and analysis. Nucleic Acids Research 31 (2003): 3784-3788.

Geysen, et al. Strategies for epitope analysis using peptide synthesis. J Immunol Methods. 102.2 (Sep. 24, 1987): 259-74.

Gruber et al., Comparative analysis of coiled-coil prediction methods. J Struct. Biol. 155 (2006): 140-5.

Gunther et al., SuperHapten: a comprehensive database for small immunogenic compounds. Nucleic Acids Research 35 (2006): D906-D910.

Hackeng, et al. Total chemical synthesis of enzymatically active human type II secretory phospholipase A2. Proc. Natl. Acad. Sci. USA 94.15 (1997): 7845-50.

Hamblett, et al., Effects of Drug Loading on the Antitumor Activity of a Monoclonal Antibody Drug Conjugate. Clinical Cancer Research 10 (2004): 7063-7070.

Hartmann-Boyce et al. Nicotine vaccines for smoking cessation (Review). Cochrane Database of Systematic Reviews 8 (2012): CD007072.

Hatsukami et al., Tobacco addiction: Diagnosis and Treatment. Lancet 371(9629):2027-2038 (2008).

Hecht et al., Recent advances in carbohydrate-based vaccines. Current Opinion in Chemical Biology 13 (2009): 354-359.

Hewitt E.W., et al., Natural processing sites for human cathepsin E and cathepsin D in tetanus toxin: implications for T cell epitope generation. The Journal of Immunology 159 (1997): 4693-4699.

Hofmann, et al. On the theoretical prediction of protein antigenic determinants from amino acid sequences. Biomed Biochim Acta. 46,11 (1987): 855-66.

Hoof, et al. NetMHCpan, a method for MHC class I binding prediction beyond humans. Immunogenetics. 61.1 (2009):1-13. doi: 10.1007/s00251-008-0341-z. Epub Nov. 12, 2008.

Hopp, TP. Retrospective: 12 years of antigenic determinant predictions, and more. Pept Res. 6.4 (Jul.-Aug. 1993): 183-90.

Hyrup, et al. Peptide Nucleic Acids (PNA): Synthesis, Properties and Potential Applications. Bioorg. Med. 4.1 (1996): 5-23.

IEDB. Free Epitope Database and Prediction Resource. IEDB.org: Free Epitope Database and Prediction Resource, www.iedb.org/.

International search report with written opinion dated Aug. 19, 2015 for PCT/US2015/027612.

Jameson et al., The antigenic index: a novel algorithm for predicting antigenic determinants. Comput Appl Biosci. 4.1 (1988): 181-6.

Jha, Save lives by counting the dead. Bulletin of the World Health Organization 88 (2010): 151-240.

Keyler D.E., et al., Enhanced immunogenicity of a bivalent incotine vaccine. International Immunopharmacology 8 (2008): 1589-1594.

Kinsey et al., Anti-drug vaccines to treat substance abuse. Biology 87.4 (2009): 309-14.

Klinman. Adjuvant activity of CpG oligodeoxynucleotides. Int Rev Immunol. 25 (2006): 135-154.

Kumar et al., ELISPOT assay for detection of peptide specific Interferiod-y secreting cells in rhesus macaques. Journal of Immunological Methods 247.1-2 (2001): 49-60.

La Rosa, et al., Clinical Evaluation of Safety and Immunogenicity of PADREOCytomegalovirus (CMV) and Tetanus-CMV Fusion Peptide Vaccines With or Without PF03512676 Adjuvant. The Journal of Infectious Diseases 205 (2012): 1294-304.

Lata et al., MHCBN 4.0: A database of MHC/TAP binding peptides and T-cell epitopes. BMC Research Notes 2 (2009): 61.

Le Sage et al., Current Status of Immunologic Approaches to Treating Tobacco Dependence: Vaccines and Nicotine-Specific Antibodies. 8 (2006): E65-75.

Lutzner et al., Quantifying Cathepsin S Activity in Antigen Presenting Cells Using a Novel Specific Substrate. Journal of Biological Chemistry 283 (2008): 36185-36194.

Matta et al., Guidelines on nicotine dose selection for in vivo research. Psychopharmacology 190 (2007): 269-319.

McCluskie et al., Enhancing immunogenicity of a 3'aminomethylnicotine-DT-conjugate anti-nicotine vaccine with CpG adjuvant in mice and non-human primates. Int Immunopharmacol. 16 (2013): 50-56.

Menendez-Arias, et al. A Basic microcomputer program for prediction of B and T cell epitopes in proteins. Comput Appl Biosci. 6.2 (Apr. 1990): 101-5.

Merrifield et al. Solid Phase Peptide Synthesis I. J Am Chem Soc 85:2149-2154 (1963).

Mifsud et al., TLR agonists as modulators of the innate immune response and their potential as agents against infectious disease. Frontiers in Immunology 5 (2014): 79.

(56) References Cited

OTHER PUBLICATIONS

Miller et al. Novel Anti-Nicotine Vaccine Using a Trimeric Coiled-Coil Hapten Carrier. PLoS One. 9.12 (Dec. 10, 2014): e114366.
Miranda, et al. Accelerated chemical synthesis of peptides and small proteins. Proc Natl Acad Sci U S A. 96.4 (Feb. 16, 1999): 1181-6.
Moreno et al., A Critical Evaluation of a Nicotine Vaccine within a Self-Administration Behavioral Model. Molecular Pharmaceutics 7 (2010): 431-41.
Moreno et al., Immunopharmacotherapy: Vaccination strategies as a treatment for drug abuse and dependence. Pharmacology, Biochemistry, and Behavior 92 (2009): 199-205.
Mullen et al., Phase 1 Trial of AMA1-C1/Alhydrogel plus CPG 7909: An Asexual Blood-Stage Vaccine for Plasmodium falciparum Malaria. PLOS ONE 3 (2008): e2940.
Muller., [43] Determination of affinity and specificity of anti-hapten antibodies by competitive radioimmunoassay. Methods in Enzymology 92 (1983): 589-601.
Nagorsen et al., Immunological monitoring of cancer vaccine therapy. Expert Opin. Biol. Ther. 4 (2004): 1677-84.
Nakai, et al. PSORT: a program for detecting sorting signals in proteins and predicting their subcellular localization. Trends Biochem Sci. 24.1 (1999): 34-6.
Office of the Surgeon General (US). The Health Consequences of Smoking: A Report of the Surgeon General. Atlanta (GA): Centers for Disease Control and Prevention (US); 2004.
Oyarzun et al., PREDIVAC: CD4+ T-cell epitope prediction for vaccine design that covers 95% of HLA class II DR protein diversity. BMC Bioinformatics 14 (2013): 52.
Parry et al., Fifty years of coiled-coils and alpha-helical bundles: a close relationship between sequence and structure. J Struct. Biol. 163 (2008): 258-69.
Pearson, et al. Improved Tools for Biological Sequence Comparison. Proc. Nat'l Acad. Sci. USA. 85 (1988): 2444-48.
Pentel et al. Chapter Fourteen—New Directions in Nicotine Vaccine Design and Use. Advances in Pharmacology 69 (2014): 553-80.
Perry-O'Keefe, et al. Peptide nucleic acid pre-gel hybridization: an alternative to southern hybridization. Proc Natl Acad Sci U S A. 93.25 (Dec. 10, 1996): 14670-5.
Persing et al. Taking toll: lipid A mimetics as adjuvants and immunomodulators. Trends Microbiol 10 (2002): S32-S37.
Pobre et al., Carrier priming or suppression: Understanding carrier priming enhancement of anti-polysaccharide antibody response to conjugate vaccines. Vaccine 32 (2014): 1423-1430.
Polosa et al., Treatment of nicotine addiction: present therapeutic options and pipeline developments. Trends in Pharmacology Sciences 32 (2011): 281-9.
Pryde et al., Selection of a Novel Anti-Nicotine Vaccine: Influence of Antigen Design on Antibody Function in Mice. PLOS ONE 8 (2013): e76557.
Raman. Design and analysis of peptide based nanoparticles. The University of Basel, Doctoral dissertation, May 2008 [online].
Ramensee et al. SYFPEITHI: database for MHC ligands and peptide motifs. Immunogenetics 50 (1999): 213-219.
Raupach et al., Nicotine Vaccines to Assist with Smoking Cessation. Drugs 72 (2012): e1-16.
Rosenberg et al., Suppression of Nicotine-Induced Pathophysiology by an Adenovirus Hexon-Based Antinicotine Vaccine. Human Gene Therapy 24 (2013): 595-603.
Saade, Fadi, et al., Pushing the frontiers of T-cell vaccines: accurate measurement of human T-cell responses. Expert Review of Vaccines 11 (2012): 1459-70.
Saha et al., Bcipep: A database of B-cell epitopes. BMC Genomics 6 (2005): 79.
Sant et al., Immunodominance in CD4 T-cell responses: implications for immune responses to influenza virus and for vaccine design. Expert Review of Vaccines 6 (2007): 357-68.
Sant et al., The control of specificity of CD4 T cell responses: thresholds, breakpoints, and ceilings. Frontiers in Immunology 4 (2013): 340.
Schnolzer, et al. In situ neutralization in Boc-chemistry solid phase peptide synthesis. Rapid, high yield assembly of difficult sequences. Int J Pept Protein Res. 40.3-4 (Sep.-Oct. 1992): 180-93.
Seligman et al., Influence of solid-phase antigen in competition enzyme-linked immunosorbent assays (ELISAs) on calculated antigen-antibody dissociation constants. Journal of Immunology Methods 168 (1994): 101-10.
Singh et al., HaptenDB: a comprehensive database of haptens, carrier proteins and anti-hapten antibodies. Bioinformatics, 22 (2006): 253-255.
Singh et al., Improved Method for Linear B-Cell Epitope Prediction Using Antigen's Primary Sequence. PLOS ONE 8 (2013): e62216.
Singh, et al. ProPred: Prediction of HLA-DR binding sites. Bioinformatics. 17 (2001): 1236-1237.
Smahel, M., et al., The effect of helper epitopes and cellular localization of an antigen on the outcome of gene gun DNA immunization. Gene Therapy 21 (2014): 225-232.
Stead et al., Cochrane Database of Systematic Reviews 1:CD000146, 2008.
Steinhagen, et al., TLR-based immune adjuvants, Vaccine, Elsevier Ltd, GB, 29.17 (Aug. 14, 2010): 3341-3355.
Stevens., Modification of an Elisa-Based procedure for affinity determination: correction necessary for use with bivalent antibody. Molecular Immunology 24 (1987): 1055-60.
Stoute et al., A Preliminary Evaluation of a Recombinant Circumsporozoite Protein Vaccine against Plasmodium falciparum Malaria. The New England Journal of Medicine 336 (1997): 86-91.
Sturniolo, T. et al., Generation of tissue-specific and promiscuous HLA ligand databases using DNA microarrays and virtual HLA class II matrices. Nat. Biotech. 17 (1999): 555-561.
Sun et al., Bioinformatics Resources and tools for conformational B-Cell Epitope Prediction. Computational and Mathematical Methods in Medicine vol. 2013 (2013): Article ID 943636.
Tonstad et al., Niccine®, a Nicotine Vaccine, for Relapse Prevention: A Phase II Randomized, Placebo-Controlled, Multicenter Clinical Trial. Nicotine & Tobacco Research 15 (2013): 1492-501.
Verma et al., Induction of a cellular immune response to a defined T-cell epitope as an insert in the flagellin of a live vaccine strain of *Salmonella*. Vaccine 13 (1995): 235-44.
Vigneron et al., Database of T cell-defined human tumor antigens: the 2013 update. Cancer Immunology Research 13 (2013): 15.
Wagner. On the interaction between proteins and nanoparticles: Coiled coil peptides organize nanoparticles and vice versa. Free University Berlin, Doctoral disseration, Jan. 2010 [online].
Walshaw et al., SOCKET: a program for identifying and analyzing coiled-coil motifs within protein structures. Journal of Molecular Biology 307 (2001): 1427-50.
Wan et al., SVRMHC prediction server for MHC-binding peptides. BMC Bioinformatics 7 (2006): 463.
Wang et al., Peptide binding predictions for HLA DR, DP and DQ molecules. BMC Bioinformatics 11 (2010): 568.
Weidermann et al., Vaccination for the prevention and treatment of breast cancer with special focus on Her-2/neu peptide vaccines. Breast Cancer Res. Treat 138 (2013): 1-12.
Woolfson et al. The Design of Coiled-Coil Structures and Assemblies, Advances in Protein Chemistry, 70 (2005): 79.
Yamada et al., Next-generation peptide vaccines for advanced cancer. Cancer Science 104 (2013): 15-21.

\* cited by examiner

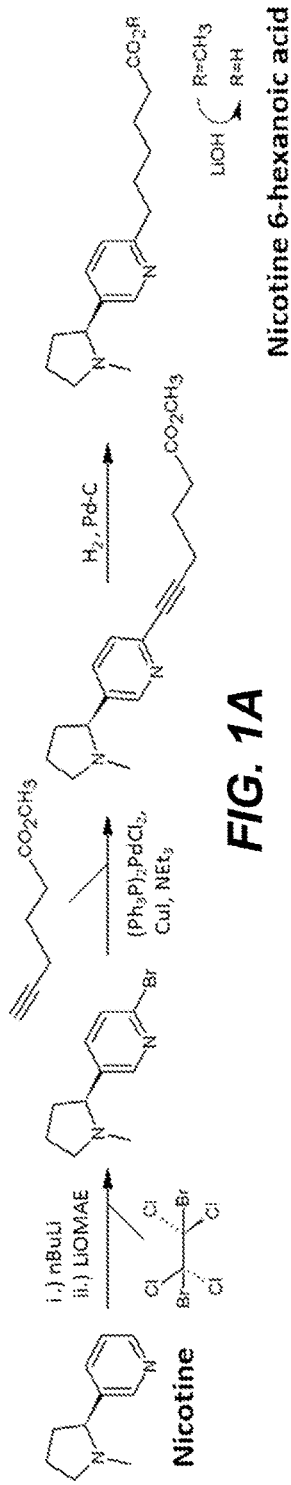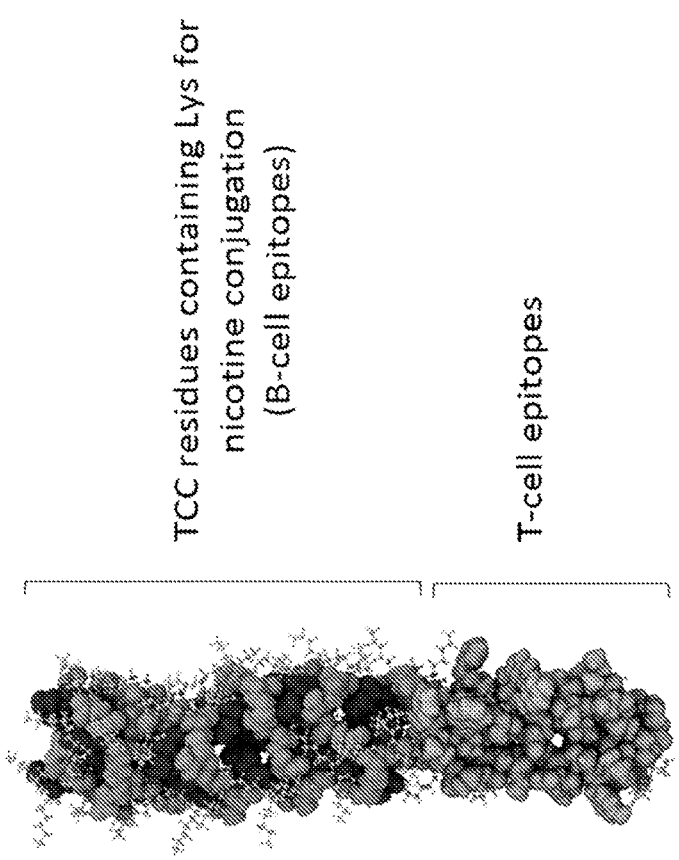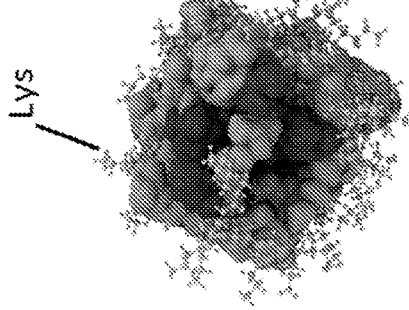
FIG. 1A
FIG. 1B

TCC sequence: KKKIEKR IEKIEKR IKKIEKR IKKIEKR IKK (SEQ ID NO:1)
Heptad position: bcdefg abcdefg abcdefg abcdefg abc

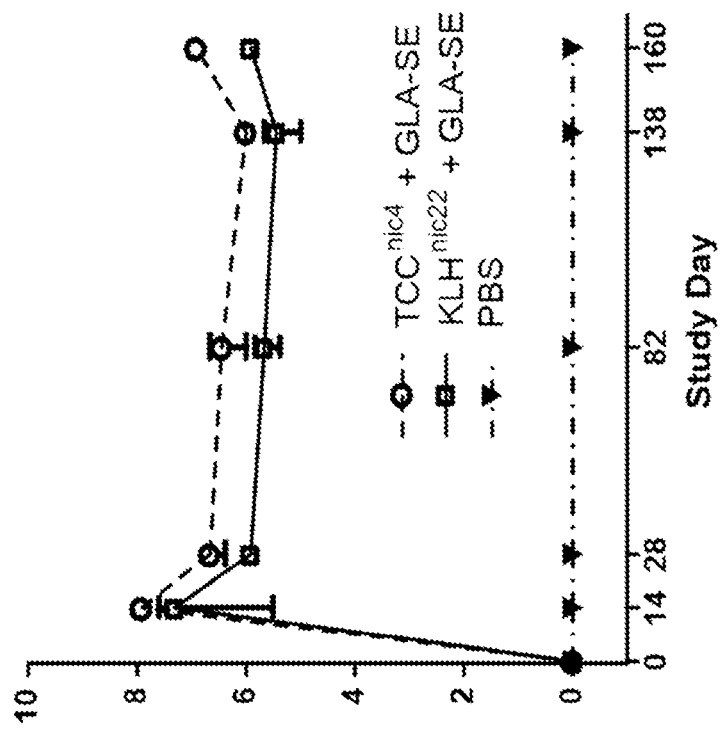
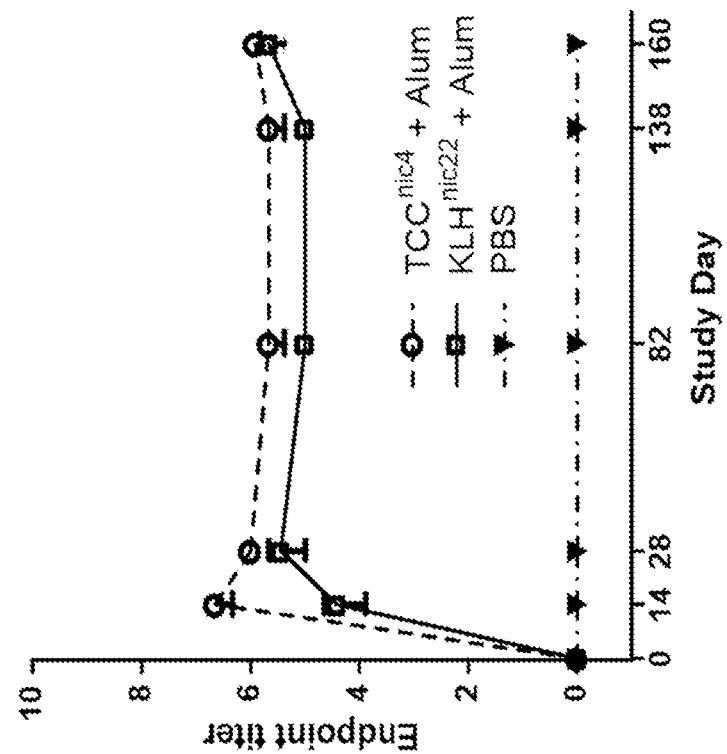
FIG. 3B
FIG. 3A

| Vaccine Group | Kd (nM) (n=5) | Std Dev. (± mean) |
|---|---|---|
| TCC<sup>nic4</sup> | 7.225 | 9.253 |
| TCC<sup>nic4</sup> + Alum | 10.43 | 10.96 |
| TCC<sup>nic4</sup> + GLA-SE | 0.8294 | 0.568 |
| KLH<sup>nic22</sup> | 442.9 | 571.2 |
| KLH<sup>nic22</sup> + Alum | 18.94 | 19.14 |
| KLH<sup>nic22</sup> + GLA-SE | 15.56 | 15.13 |

# SYNTHETIC HAPTEN CARRIER COMPOSITIONS AND METHODS

CROSS REFERENCE TO RELATED APPLICATIONS

This application is a U.S. National Phase application under 35 U.S.C. § 371 of International Application No. PCT/US2015/027612, filed Apr. 24, 2015, which claims the benefit of U.S. Provisional Application No. 61/984,629, filed Apr. 25, 2014, which are incorporated herein by reference in their entireties.

STATEMENT OF GOVERNMENT INTEREST

This invention was made with government support under Contract No. R43 DA033845-01 awarded by National Institute on Drug Abuse, of the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 910210_402USPC_SEQUENCE_LISTING. The text file is 7.1 KB, was created on Oct. 24, 2016, and is being submitted electronically via EFS-Web.

BACKGROUND

Technical Field

The present disclosure relates to peptide monomers, dimers, and trimers that may be used as synthetic hapten carrier molecules for vaccines.

Description of the Related Art

Nicotine, cocaine, heroin, and most drugs of abuse are haptens, which are non-immunogenic. Haptens are typically coupled to peptide carriers to enhance their immunogenicity. Peptide carriers recruit the involvement of CD4+ T cells in the activation of hapten-specific antibody producing B cells. Other antigens, such as peptides, lipids, nucleic acids, and carbohydrates, due to their lack of complexity or small size, are ineffective immunogens themselves. These small or non-complex antigens must also be conjugated with carrier peptides to evoke specific antibody responses. Immunization for generating of anti-hapten antibodies is important for the development of alternative prophylactics and therapies for drug addiction, infectious diseases, cancer, allergies, and other disease and disorders.

Tobacco addiction is the single predominant cause of cancer and heart disease, resulting in an estimated 5 million deaths a year (see, e.g., Jha, 2010, Bulletin of the World Health Organization 88:151-240). The health risks and economic burden to society and health care systems associated with smoking are clear and undeniable. Each year in the U.S. nearly half of the 46 million smokers attempt to quit, yet due to the highly addictive nature of nicotine, less than 5% succeed (The consequences of smoking: a report of the Surgeon's General, USA, 2004 located at the Internet at the web site for the surgeon general, surgeongeneral.gov/library/smokingconsequences/; Fiore et al., 2000, Treating Tobacco Use and Dependence, Quick Reference Guide for Clinicians, located at the Internet at the website for the surgeon general, surgeongeneral.gov/tobacco/tobaqrg.htm). Aids to smoking cessation include supportive counseling, nicotine replacement (gums, patches, etc.), and receptor antagonists that reduce nicotine reward and withdrawal symptoms. Unfortunately, long-term outcomes for nicotine replacement therapies remain poor and achieve an abstinence rate of only 12-22% after the first year (see, e.g., Hatsukami et al., 2008, Lancet, 371:2027-38; Stead et al., 2008, Cochrane Database of Systematic Reviews 1:CD000146). There is a clear need to neutralize the nicotine "high" in order to help smokers overcome their addiction.

One approach to reduce nicotine addiction has been to prepare nicotine vaccines. While nicotine vaccines have shown promise in mice, rats, and non-human primates in their ability to sequester nicotine within the blood and to diminish nicotine-mediated physiological and behavioral responses including nicotine craving (see, e.g., Polosa and Benowitz, 2011, *Trends in Pharmacological Sciences:* 32:281-9; Raupach and Hoogsteder, 2012, *Drugs* 72:e1-16), the concept is not yet proven in humans. Results from four randomized studies indicated that the vaccines were safe, but no significant difference in smoking abstinence was observed between the intervention and placebo groups (see, e.g., Hartmann-Boyce et al., 2012, *Cochrane Database Syst. Rev.* 8:CD007072).

There is a need in the art for vaccines that induce an optimal immune response to nicotine and other drugs of abuse and to other less immunogenic antigens.

BRIEF SUMMARY

Embodiment 1

A peptide monomer comprising: (a) an amphipathic α-helical peptide comprising an amino acid sequence with at least 80% identity to SEQ ID NO:1, SEQ ID NO:2, or SEQ ID NO:3; and, optionally (b) at least one T cell epitope peptide linked to the C-terminus of the amphipathic α-helical peptide.

Embodiment 2

The peptide monomer of embodiment 1, wherein the amphipathic α-helical peptide comprises an amino acid sequence according to the formula: (E or X)XIEXR-[I(E or X)XIEXR]$_n$-I(E or X)X, wherein X=K for each instance; or each X is independently selected from D and E; and n=3, 4, 5, 6, 7, 8, 9, or 10.

Embodiment 3

The peptide monomer of embodiment 1, comprising an amino acid sequence with at least 90% identity to SEQ ID NO:1, SEQ ID NO:2, or SEQ ID NO:3.

Embodiment 4

The peptide monomer of embodiment 1, comprising an amino acid sequence of SEQ ID NO:1, SEQ ID NO:2, or SEQ ID NO:3.

Embodiment 5

The peptide monomer of embodiment 2, wherein n=4, 5, 6, 7, or 8.

Embodiment 6

The peptide monomer according to any one of embodiments 1-5, wherein the at least one T cell epitope peptide is a CD4$^+$ T cell epitope peptide

Embodiment 7

The peptide monomer of embodiment 6, wherein the CD4$^+$ T cell epitope peptide is a promiscuous CD4$^+$ T cell epitope peptide.

Embodiment 8

The peptide monomer of embodiment 7, wherein the promiscuous CD4$^+$ T cell epitope peptide comprises the amino acid sequence set forth in SEQ ID NO:10.

Embodiment 9

The peptide monomer of according to any one of embodiments 1-7, wherein the at least one T cell epitope peptide is a T cell epitope peptide of a pathogenic microorganism.

Embodiment 10

The peptide monomer of embodiment 9, wherein the at least one T cell epitope peptide is an influenza hemagglutinin T cell epitope peptide.

Embodiment 11

The peptide monomer of embodiment 10, wherein the at least one T cell epitope peptide comprises the amino acid sequence set forth in SEQ ID NO:6.

Embodiment 12

The peptide monomer according to any one of embodiments 1-11, wherein at least two T cell epitope peptides are fused in series to the C-terminus of the amphipathic α-helical peptide.

Embodiment 13

A peptide dimer comprising two peptide monomers according to any one of embodiments 1-12.

Embodiment 14

A trimeric coiled-coil peptide comprising: three peptide monomers according to any one of embodiments 1-12.

Embodiment 15

A peptide carrier conjugate comprising the peptide monomer of any one of embodiments 1-12, the peptide dimer of embodiment 13, or the trimeric coiled-coil peptide of embodiment 14 linked to a hapten, wherein the hapten is linked to a lysine or aspartic acid residue of the peptide monomer.

Embodiment 16

The peptide carrier conjugate of embodiment 15, wherein the hapten is a drug of abuse.

Embodiment 17

The peptide carrier conjugate of embodiment 16, wherein the drug of abuse is nicotine or an analog thereof.

Embodiment 18

The peptide carrier conjugate of embodiment 16, wherein the drug of abuse is cocaine, methamphetamine, morphine, cannabinoid, or an analog thereof.

Embodiment 19

The peptide carrier conjugate of embodiment 17, wherein the nicotine analog is nicotine 6-hexanoic acid.

Embodiment 20

The peptide carrier conjugate according to any one of embodiments 15-19, wherein peptide carrier conjugate is linked to at least two haptens.

Embodiment 21

The peptide carrier conjugate of embodiment 20, wherein the at least two haptens are selected from nicotine, nicotine analogs, and structurally distinct nicotine haptens.

Embodiment 22

An immunogenic composition comprising the peptide carrier conjugate according to any one of embodiments 15-21; and a pharmaceutically acceptable carrier, wherein the composition induces an immune response specific for the hapten.

Embodiment 23

The immunogenic composition of embodiment 22, wherein the immunogenic composition further comprises at least one T cell epitope peptide.

Embodiment 24

The immunogenic composition of embodiment 23, wherein the T cell epitope peptide is a CD4$^+$ T cell epitope peptide.

Embodiment 25

The immunogenic composition of embodiment 24, wherein the CD4$^+$ T cell epitope peptide is a promiscuous CD4$^+$ T cell epitope peptide.

Embodiment 26

The immunogenic composition of embodiment 25, wherein the promiscuous CD4$^+$ T cell epitope peptide comprises the amino acid sequence set forth in SEQ ID NO:10.

Embodiment 27

The immunogenic composition according to any one of embodiments 23-25, wherein the at least one T cell epitope peptide is a T cell epitope peptide of a pathogenic microorganism.

Embodiment 28

The immunogenic composition of embodiment 27, wherein the at least one T cell epitope peptide is an influenza hemagglutinin T cell epitope peptide.

Embodiment 29

The immunogenic composition of embodiment 28, wherein the at least one T cell epitope peptide comprises the amino acid sequence set forth in SEQ ID NO:6.

Embodiment 30

The immunogenic composition according to any one of embodiments 22-29, further comprising a pharmaceutically acceptable adjuvant.

Embodiment 31

The immunogenic composition of embodiment 30, wherein the adjuvant is a toll-like receptor (TLR) agonist.

Embodiment 32

A method of inducing an immune response specific for a hapten in a subject, comprising administering to the subject the immunogenic composition according to any one of embodiments 22-31.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." In addition, the term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. Headings provided herein are for convenience only and do not interpret the scope or meaning of the claimed embodiments.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise. Thus, for example, reference to "a non-human animal" may refer to one or more non-human animals, or a plurality of such animals, and reference to "a cell" or "the cell" includes reference to one or more cells and equivalents thereof (e.g., plurality of cells) known to those skilled in the art, and so forth. When steps of a method are described or claimed, and the steps are described as occurring in a particular order, the description of a first step occurring (or being performed) "prior to" (i.e., before) a second step has the same meaning if rewritten to state that the second step occurs (or is performed) "subsequent" to the first step. The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise. The term, "at least one," for example, when referring to at least one compound or to at least one composition, has the same meaning and understanding as the term, "one or more."

BRIEF DESCRIPTION OF THE DRAWINGS

FIGS. 1A-D: FIG. 1A shows a reaction scheme for preparing derivatized nicotine with hexanoic acid at the 6-position of the pyridine ring. FIG. 1B presents a molecular model of a trimeric coiled-coil (TCC) peptide containing three amphipathic helices (6.2 kDa each) and that comprises lysine residues. Lysine residues (see arrow pointing to side chains) are solvent exposed for hapten conjugation. The hydrophobic component of the helices is shown as dark gray Van der Waals spheres. The C-terminal portion of the molecule optionally contains a CD4 T-cell epitope that induces B-cell help and durable antibody responses. FIG. 1C presents a molecular model of a TCC peptide containing three amphipathic helices comprising aspartic acid residues (see arrow pointing out side chains), which are solvent exposed for hapten conjugation. The hydrophobic component of the helices is shown as dark gray Van der Waals spheres. The C-terminal portion of the molecule contains a CD4 T-cell epitope that induces B-cell help and durable antibody responses. FIG. 1D illustrates an example of a peptide monomer amino acid sequence (SEQ ID NO:1) conforming to heptad repeat formation, solvent exposure of the charged lysine residues, and interactions among the peptide monomers in the trimeric coiled coil structure.

FIG. 2A presents a graph showing the number of amino acids in several hapten carriers: keyhole limpet hemocyanin (KLH); Exotoxoid A (ExoT A); diphtheria toxoid (Diph T): and tetanus toxoid (Tet T) compared with a TCC comprising lysine residues. The number of lysines available for hapten conjugation in each carrier is reported above the bar. FIG. 2B shows the percent lysines in each carrier protein.

FIGS. 3A-B illustrate anti-nicotine antibody titers as measured by ELISA. C57Bl/6 mice (n=5/group) were immunized (days 0, 14, and 146) with 2.5 μg of the trimeric coiled-coil peptide vaccine comprising peptide monomers with 16 lysines conjugated to an average of 4 nicotines per monomer. Control groups were administered KLH-Nic22 or PBS. Vaccines were formulated with (A) Alum adjuvant or (B) GLA-SE adjuvant. Sera were collected at the indicated times and assayed for anti-nicotine antibodies by ELISA.

DETAILED DESCRIPTION

Figure 1C:
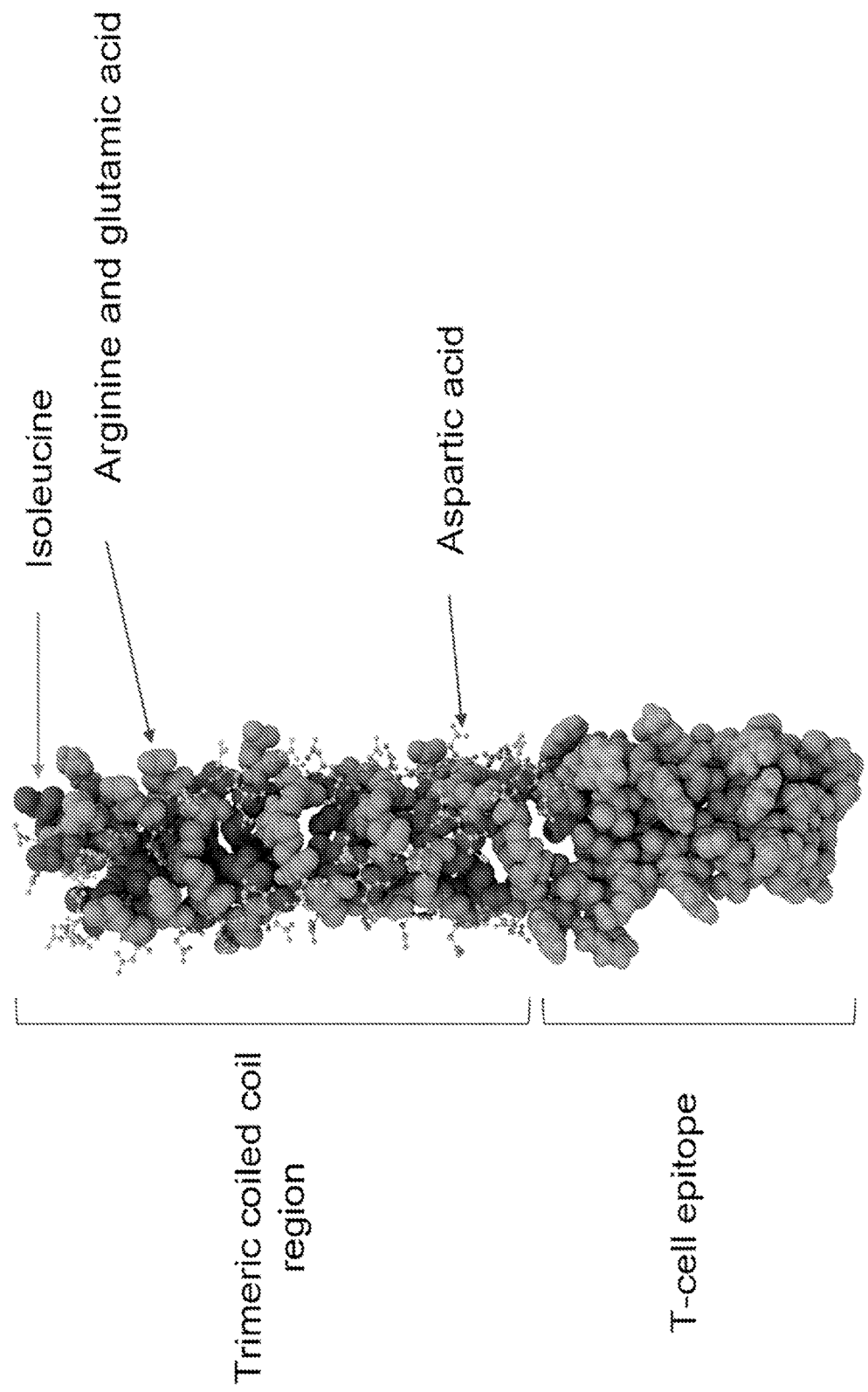

Inducing an adequate immune response to haptens, including small molecules, peptides, and other poorly immunogenic substances in subjects, particularly human subjects, has been challenging. Provided herein are peptide monomers or dimers or trimers assembled therefrom that can be used as carrier molecules for evoking a robust immune response to a hapten. The monomeric, dimeric, or trimeric peptide conjugates ("peptide carrier conjugates") are useful for vaccine compositions in methods for the prevention or treatment of drug addiction, disease, infection, cancer, or poisoning.

By way of background and example, nicotine vaccines induce high affinity antibodies that block nicotine from crossing the blood-brain barrier and stimulating a psychoactive response; however, the studies with nicotine vaccines to date have not demonstrated significant success. Conceivably, a nicotine vaccine would reduce relapse rates over time since the antibody response can last for months or years and would produce fewer side effects than current anti-smoking medications, and the vaccines could be combined safely with other therapies (see, e.g., Kinsey et al., 2009, *Biology* 87:309-14; Le Sage et al., 2006, 8:E65-75; Moreno and Janda, 2009, *Pharmacol. Biochem. Behav.* 92:199-205). Nicotine vaccines have shown promise in mice, rats, and non-human primates in their ability to sequester nicotine within the blood and to diminish nicotine-mediated physiological and behavioral responses including nicotine craving (see, e.g., Polosa and Benowitz, 2011, *Trends in Pharmacological Sciences* 32:281-9; Raupach and Hoogsteder, 2012, *Drugs* 72:e1-16). However, the concept is not yet proven in humans as evidenced by four randomized studies involving 2,642 subjects who smoked a minimum often cigarettes a day and were motivated to quit (see, e.g., Hartmann-Boyce et al., 2012, *Cochrane Database Syst. Rev.* 8:CD007072). These subjects received monthly vaccinations for six months in addition to counseling; after one year, abstinence was assessed biochemically by measuring exhaled carbon monoxide. While these vaccines appeared safe, no significant difference in smoking abstinence was detected between the intervention and placebo groups.

The general ineffectiveness of clinical-stage nicotine vaccines to date has fostered a re-evaluation of the requirements for efficacy. Nicotine delivery kinetics to the brain appear to be crucial in promoting addiction, and high levels of nicotine reach the human brain within 10-20 seconds after smoke inhalation (see, e.g., Pentel and LeSage, 2014, *Adv. Pharmacol.* 69:553-80). Consequently, to prevent nicotine from reaching the brain, a vaccine needs to induce serum antibodies with a nicotine binding capacity that exceeds inhaled amounts. This functional measure of nicotine binding capacity is dependent on both antibody quantity (e.g., determined by titer) and quality (e.g., affinity).

A problem with generating an antibody response to nicotine and other drugs of abuse is that the drugs are non-immunogenic due to their small size. Consequently, they must be conjugated as a hapten to a carrier (e.g., a protein) that serves as a scaffold for antigen presentation. These carriers may also provide peptide epitopes that induce T-cell mediated B cell proliferation, antibody class switching, and the establishment of B cell memory. To date, preclinical and clinical stage hapten carriers are typically derived from microbial sources like tetanus toxioid, diphtheria toxoid, and *Pseudomonas* exotoxoid A (see, e.g., Polosa et al., 2011, *Trends Pharmacol. Sci.* 32:281-9; Raupach et al., 2012, *Drugs* 72:e1-16; Pentel and LeSage, 2014, *Adv. Pharmacol.* 69:553-80; and Tonstad et al., *Nicotine Tob. Res.* 2013, 15:1492-501). However, these carriers share several limitations. For instance, the number of haptens bound per carrier protein in these constructions is dictated by the number of lysine residues that are used for chemical conjugation. Consequently, the maximum number of nicotine molecules is typically limited to less than 50. Thus, the amount of nicotine relative to the carriers used to date is quite low, which necessitates the need for large vaccine doses. Also, the stoichiometry and spacing of each lysine varies between commonly used carriers, and uncertainty remains about which linkages make the best epitope for stimulating high avidity antibody titers. Another major problem is that these carriers are highly immunogenic and induce anti-carrier antibodies that could neutralize and limit booster vaccination efficacy over time. In fact, "epitopic suppression" is a widely recognized phenomenon first observed with licensed polysaccharide conjugate vaccines that also utilize tetanus and diphtheria toxin carriers (see, e.g., Pobre et al., 2014, *Vaccine* 32:1423-1430). Not surprisingly, anti-carrier antibody responses are higher when the amount of conjugated hapten is low, and increasing hapten density on the carrier protein was found to reduce epitopic suppression.

To circumvent the problems associated with current nicotine vaccines, described herein are synthetic hapten carriers that can be used for any drug of abuse vaccine including nicotine. One embodiment of a carrier is a relatively short trimeric coiled-coil peptide (TCC) comprising three monomers of amphipathic α-helical peptides (see FIGS. 1B-1D) that can be formulated, if desired, with any adjuvant of choice. The basic unit of each peptide monomer is a repeating heptad peptide sequence rich in either lysine and isoleucine residues, or the acidic amino acids, aspartic acid and glutamic acid each alone or in any combination, and isoleucine residues. Following assembly of the peptide monomers into the trimeric coiled-coil peptide, the charged lysine or aspartic acid or glutamic acid residues become solvent-exposed along the helix surface, and the repeating isoleucine residues form a hydrophobic core along the length of the carrier. Arginine and glutamic acid residues within the repeating heptad peptide are strategically placed to form salt bridges between adjacent helices to further stabilize the trimeric structure. This design creates a readily accessible conformation for hapten conjugation and, in stark contrast to a natural hapten carrier, a series of hapten-derived B-cell epitopes with uniform stoichiometry and spacing that can be used to optimize hapten structure. Consequently, this trimeric coiled-coil peptide conjugate contains a much higher density of hapten molecules linked to the carrier compared to other carrier proteins, which is a key determinant of immunogenicity. Moreover, the increased hapten frequency relative to the uncharged hydrophobic core directs B cell responses to the hapten rather than the carrier, thereby limiting anti-carrier antibody responses (see, e.g., Pobre et al., 2014, *Vaccine* 32:1423-1430). Each peptide monomer optionally includes at least one T cell epitope linked to the N- or C-terminus of the amphipathic α-helical peptide. A T cell epitope may be, for example, a CD4$^+$ T cell epitope, which enhances development of memory B cells and plasma cells that produce high affinity antibodies (see, e.g., Sant et al., 2007, *Expert Rev. Vaccines* 6:357-68; Sant et al., 2013, *Front. Immunol.* 4:340).

Provided herein are peptide monomers comprising an amphipathic α-helical peptide comprising an amino acid sequence according to the formula: (E or X)XIEXR-[I(E or X)XIEXR]$_n$-I(E or X)X, wherein X=K for each instance, or each X is independently selected from D and E, and n=1, 2, 3, 4, 5, 6, 7, 8, 9, 10, 11, 12, 13, 14, 15, 16, 17, 18, 19, or 20; and optionally, at least one T cell or B cell epitope peptide linked to an end of the amphipathic α-helical peptide. These peptide monomers may self-assemble to form a peptide dimer, or a peptide trimer, also referred to as a trimeric coiled-coil peptide. The peptide monomer, peptide dimer, or trimeric coiled-coil peptide may be used as a carrier molecule for a hapten that is linked to a lysine or aspartic acid residue of the peptide monomer. The peptide monomer, peptide dimer, and trimeric coiled-coil peptide conjugates are useful for vaccine compositions and methods for evoking antigen specific and robust immune responses to a hapten (such as drugs of abuse, including nicotine, cocaine, methamphetamine, morphine, cannabinoid, or an analog thereof; carbohydrates; peptides; self-antigens; for example).

Peptide Monomers

A "peptide monomer" refers to a single peptide molecule, which may oligomerize with other peptide monomers to form a polymeric peptide complex (e.g., dimer, trimer, tetramer, pentamer, hexamer, heptamer, etc.). In certain embodiments, the present disclosure provides a peptide monomer comprising a) an amphipathic α-helical peptide comprising an amino acid sequence with at least 80% identity to SEQ ID NO:1, SEQ ID NO:2, or SEQ ID NO:3; and optionally b) at least one epitope peptide linked to a terminus of the amphipathic α-helical peptide. The amino acid sequences for SEQ ID NOS:1-3 are shown in Table 1.

TABLE 1

Exemplary amphipathic α-helical peptides for use in the peptide monomer

| Amino Acid Sequence | SEQ ID NO: |
|---|---|
| KKIEKRIEKIEKRIKKIEKRIKKIEKRIKKIEKRIKK | 1 |
| KKIEKRIEKIEKRIKKIEKRIKKIEKRIKKIEKRIKK IEKRIEKIEKRIKKIEKRIEKIEKRIKK | 2 |
| DDIEDRIEDIEDRIDDIEDRIDDIEDRIDDIEDRIDD | 3 |

In certain embodiments, the amphipathic α-helical peptide comprises an amino acid sequence according to the formula: (E or X)XIEXR-[I(E or X)XIEXR]$_n$-I(E or X)X, wherein X=K for each instance, or each X is independently selected from D and E, and n=1, 2, 3, 4, 5, 6, 7, 8, 9, 10, 11, 12, 13, 14, 15, 16, 17, 18, 19, or 20. This formula may also be represented by (E or K)KIEKR-[I(E or K)KIEKR]$_n$-I(E or K)K [SEQ ID NO:4] and (E or D)(E or D)IE(E or D)R-[I(E or D)(E or D)IE(E or D)R]$_n$-I(E or D)(E or D) [SEQ ID NO:5]. In certain embodiments, n=3, 4, 5, 6, 7, 8, 9, or 10; or n=4, 5, 6, 7, 8, or 9. In other particular embodiments, n=16, 17, 18, 19, or 20. The length of the amphipathic α-helical peptide will vary according to the number of heptad repeats (i.e., (n×7)+9).

Figure 1D:
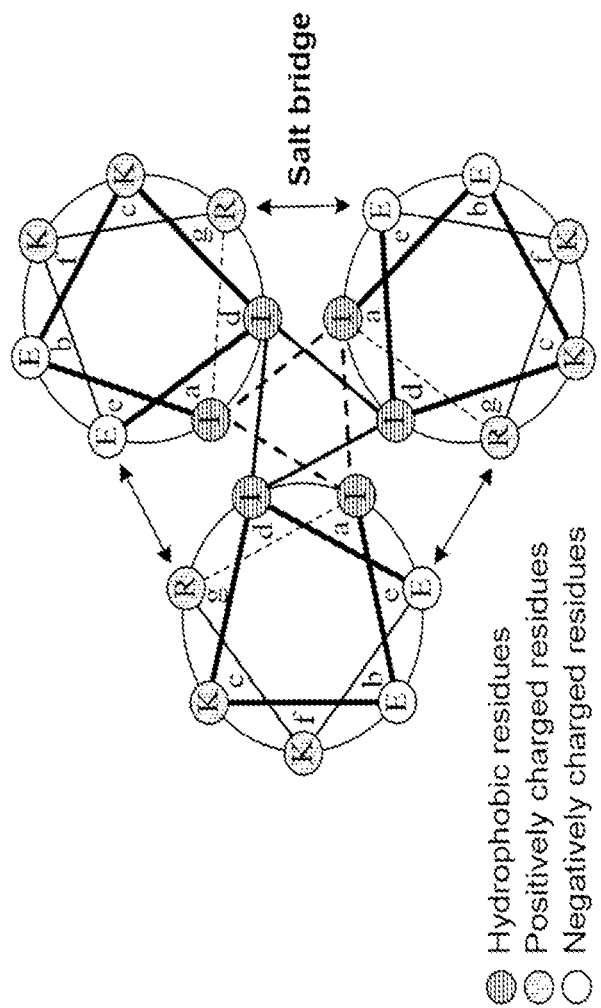
Figure 2B:
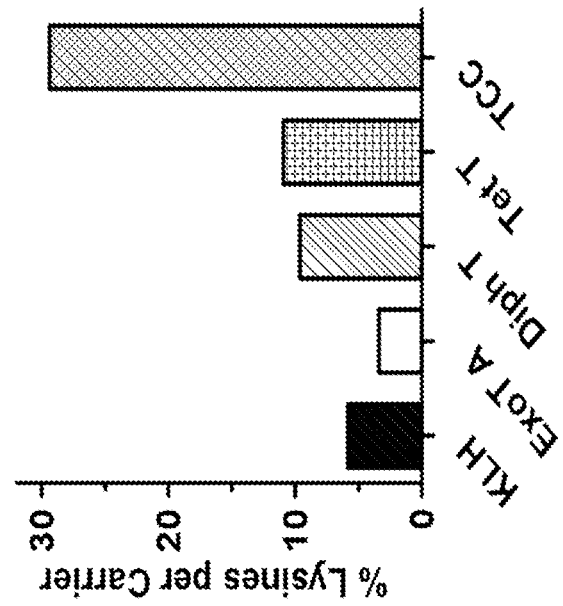
FIGS. 2A-B.
Figure 2A:
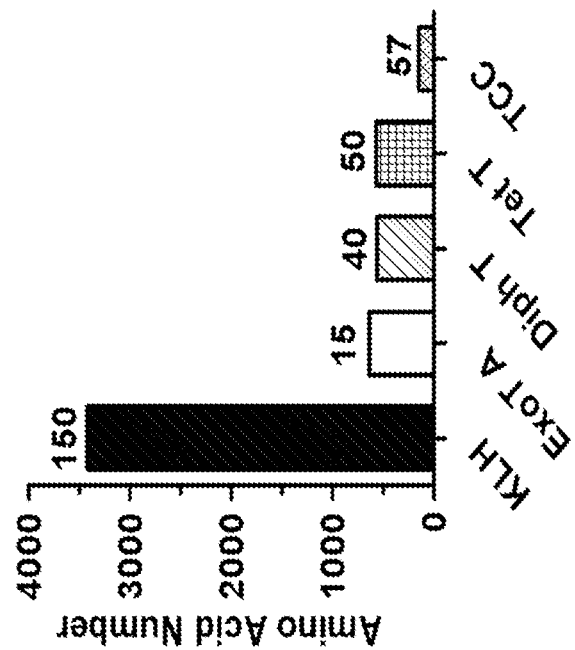

An "amphipathic α-helical peptide" refers to a peptide with an α-helical structure, where one surface of the α-helix has mainly hydrophilic amino acids and the opposite face has mainly hydrophobic or lipophilic amino acids. The amino acid sequence of an amphipathic α-helix alternates between hydrophilic and hydrophobic residues every 3 to 4 residues, as the α-helix turns every 3.6 residues (FIG. 1D). The amphipathic α-helical peptides of the present disclosure comprise a seven-residue heptad sequence rich in lysines or glutamic acids/aspartic acids, and isoleucines. For peptide monomers comprising at least two heptad sequences, each heptad sequence in the peptide is tandemly linked to another heptad sequence. In certain embodiments, between 2-15 heptad sequences are repeated in tandem in a monomer. The positions within a heptad sequence are typically denoted abcdefg. An amphipathic α-helical peptide may comprise a heptad repeat having an amino acid sequence according to the formula [I(E or X)XIEXR] where X is K for each instance, or each X is independently selected from E and D (e.g., I(E or D)DIEDR (SEQ ID NO: 16) or I(E or K)KIEKR (SEQ ID NO: 17) or IEEIEER (SEQ ID NO: 18)). In certain embodiments where each X is independently selected from E and D, every X in an amphipathic α-helical peptide may be a glutamic acid residue, every X in an amphipathic α-helical peptide may be an aspartic acid residue, or an amphipathic α-helical peptide may have both glutamic acid and aspartic acid residues. Examples of amphipathic α-helical peptides are set forth in SEQ ID NOS:1-3, which contain four (SEQ ID NO:1 and 3) or eight (SEQ ID NO:2) heptad repeats in tandem. The heptad repeats within each peptide monomer may have identical sequences or may have different sequences. The tandem heptad repeats within a peptide form an amphipathic α-helix, with a heptad repeat occurring every two turns of the helix. The amphipathic α-helical peptide may comprise incomplete heptad repeat sequences at the N- and/or C-terminus. By way of example, an amphipathic α-helical peptide may have a portion of the heptad repeat denoted by bcdefg (i.e., (E or X)XIEXR) at the N-terminus and a portion of the heptad repeat denoted by abc (i.e., I(E or X)X) at the C-terminus. A variety of N- and C-terminal sequences may be constructed by varying the length of the portion of the heptad repeat sequence used from 1 to 7 amino acids. By way of example, the N-terminus may comprise a complete or partial heptad repeat sequence as represented by abcdefg ([I(E or X)XIEXR]), bcdefg ((E or X)XIEXR), cdefg (XIEXR), defg (IEXR), efg (EXR), fg (XR), or g (R), wherein X is K for each instance, or each X is independently selected from D and E; the C-terminus may comprise a complete or partial heptad repeat sequence as represented by a (I), ab (I(E or X)), abc (I(E or X)X), abcd (I(E or X)XI), abcde (I(E or X)XIE), abcdef (I(E or X)XIEX), or abcdefg ([I(E or X)XIEXR]), wherein X is K for each instance, or each X is independently selected from D and E. The portion of the heptad repeat used at the N- or C-terminus is selected to preserve the continuity of repeating heptad pattern.

Three amphipathic α-helical peptides may spontaneously assemble to form a stable, parallel bundle of α-helical peptides (e.g., a trimeric coiled-coil). Following assembly, the charged lysines, aspartic acid and/or glutamic acid residues are solvent-exposed on the helix surface for hapten conjugation, and the repeating isoleucine residues form a hydrophobic core along the length of the trimeric coiled-coil that permit oligomerization with other helices. Arginine and glutamic acid residues are strategically placed within the repeating heptad to form salt bridges between adjacent helices to further stabilize the trimeric structure (FIG. 1D). Alternatively, two amphipathic α-helical peptides may assemble to form a peptide dimer.

In certain embodiments, the amphipathic α-helical peptide comprises an amino acid sequence with at least 70%, 75%, 80%, 85%, 90%, 95%, 99%, or 100% identity to SEQ ID NO:1, SEQ ID NO:2, or SEQ ID NO:3. In certain embodiments, the amphipathic α-helical peptide consists an amino acid sequence as set forth in SEQ ID NO:1, SEQ ID NO:2, or SEQ ID NO:3. Sequence identity refers to the degree of correspondence of two sequences in an alignment, often expressed as a percentage. Differences between two sequences may be determined by methods routinely practiced in the art to determine identity, which are designed to give the greatest match between the sequences tested. Methods to determine sequence identity can be determined by using publicly available computer programs. Computer program methods to determine identity between two sequences include, for example, BLASTP, BLASTN (see, e.g., Altschul, S. F. et al., *J. Mol. Biol.* 215: 403-410 (1990), and FASTA (see, e.g., Pearson and Lipman, *Proc. Natl. Acad. Sci. USA* 85; 2444-2448 (1988). The BLAST family of programs is publicly available from NCBI and other sources (see, e.g., *BLAST Manual*, Altschul, S., et al., NCBI NLM NIH Bethesda, Md.).

The type of residue that may be substituted at each position within the heptad repeat should maintain the α-helical structure, stability and oligomerization state of the peptide. For example, the lysine, glutamic acid, or aspartic acid residues at sites c and f, and optionally b, should be preserved to maintain frequency and spacing of the hapten conjugation sites. In another example, the isoleucine residues at sites a and d of the heptad repeat may be substituted other hydrophobic residues (e.g., Val, Ile, Leu, Met, Tyr, Phe or Trp). In another example, the arginine residue at site g of the heptad repeat and glutamic acid residues at sites b and e may be substituted with other amino acids with charged side chains that preserve the salt bridges between adjacent helices for stabilizing the trimeric structure (e.g., Asp or Glu may form inter-helical salt bridge with Lys, Arg or His). In certain embodiments, the amphipathic α-helical peptide may also contain an insertion of one, two, three, or four residues into the heptad pattern between repeats. For example, insertions of one, two, three, or four residues may occur as a single occurrence or occur multiple times in the amphipathic α-helical peptide. The insertion may occur with regularity so as to increase the repeat pattern from seven residues. A person of skill in the art would appreciate how to modify the amphipathic α-helical peptides described herein while maintaining their properties. Properties of coiled-coil structures and assemblies are known in the art and have been previously described (see, e.g., Parry et al., 2008, *J. Struct. Biol.* 163:258-69; Burkhard et al., *J. Mol. Biol.* 318:901; Burkhard et al., 2000, *Protein Sci.* 9:2294-301; Burkhard et al., 2001, Trends Cell Biol. 11:82-88; Woolfson, 2005, *Adv. Protein Chem.* 70:79-112). Coiled-coil prediction programs are also available for identifying and analyzing coiled-coil motifs (see, e.g., Walshaw and Woolfson, 2001, *J. Mol. Biol.* 307:1427-50; Gruber et al., 2006, *J. Struct. Biol.* 155:140-5).

In one embodiment, the peptide monomers form trimeric coiled-coils. In alternative embodiments, the peptide monomers may assemble to form dimeric, tetrameric, pentameric, hexameric, and heptameric coiled-coil peptides. In yet further embodiments, the peptide is used as a carrier in monomeric form.

Peptides and polypeptides may be chemically synthesized by manual techniques or by automated procedures. Equipment for automated synthesis of peptides and polypeptides is commercially available (e.g., Perkin-Elmer, Inc.; Applied BioSystems Division, Foster City, Calif.), and may be operated according to the manufacturer's instructions. Solid phase polypeptide synthesis has been performed since the early 1960's (see, e.g., Merrifield, *J. Am. Chem. Soc.* 85:2149-2154 (1963)). Numerous improvements to synthesis methods have been developed, and many methods have been automated and chemistries have been developed to protect terminal ends and other reactive groups (see, e.g., Geysen et al., *J. Immun. Meth.* 102:259-274 (1987); Miranda et al., *Proc. Natl. Acad. Sci. USA* 96:1181-86 (1999); Frank et al., *Tetrahedron* 44:6031-6040 (1988); Hyrup et al., *Bioorg. Med. Chem.* 4:5-23 (1996); Perry-O'Keefe et al., *Proc. Natl. Acad. Sci. USA* 93:14670-675 (1996); Schnölzer, et al. *Int. J. Pept. Protein Res.* 40, 180-193 (1992); Hackeng et al., *Proc. Natl. Acad. Sci. USA* 94:7845-50 (1997); Creighton, T. E. Protein: Structures and Molecular Properties, pp. 55-60, W. H. Freeman and Co., New York, N.Y. (1984)). Synthesized peptide monomers may be obtained from any number of different custom peptide synthesizing manufacturers. If required, synthesized peptides or polypeptides may be purified using any number of methods routinely practiced in the art, such as preparative reverse phase chromatography, partition chromatography, gel filtration, gel electrophoresis, or ion-exchange chromatography or other methods used in the art.

Alternatively, the peptide monomers may be recombinantly produced using methods routinely practiced in the molecular biology art. Selection of the appropriate vector and expression control sequences (e.g., a promoter) and preparation of certain recombinant expression constructs is well within the level of ordinary skill in the art. The expression vector also comprises expression control sequences, such as a promoter, enhancer, initiation site, and the like that are selected depending on the vector and host cell used to produce the peptide monomer. The nucleotide sequence encoding a peptide in the expression vector is operatively linked to at least one appropriate expression control sequences (e.g., a promoter or a regulated promoter) to direct mRNA synthesis.

A polynucleotide that encodes the peptide monomer may be incorporated into a recombinant expression vector for production of the respective peptide in a host cell. Host cells containing recombinant expression constructs may be genetically engineered (transduced, transformed, or transfected) with the vectors and/or expression constructs (for example, a cloning vector, a shuttle vector, or an expression construct). The vector or construct may be in the form of a plasmid, a viral particle, a phage, etc. The engineered host cells can be cultured in conventional nutrient media modified as appropriate for activating promoters, selecting transformants, or amplifying particular genes or encoding-nucleotide sequences. Selection and maintenance of culture conditions for particular host cells, such as temperature, pH and the like, will be readily apparent to the ordinarily skilled artisan. In general, the desired host cell is one that can be adapted to sustained propagation in culture to yield a stable cell line that can express sufficient amount of the peptide monomer.

Representative examples of such expression control sequences include LTR or SV40 promoter, *E. coli* lac or trp, the phage lambda $P_L$ promoter, and other promoters known to control expression of genes in prokaryotic or eukaryotic cells or their viruses. Promoter regions can be selected from any desired gene using CAT (chloramphenicol transferase) vectors or other vectors with selectable markers. Particular bacterial promoters include lacI, lacZ, T3, T5, T7, gpt, lambda $P_R$, $P_L$, and trp. Eukaryotic promoters include CMV immediate early, HSV thymidine kinase, early and late SV40, LTRs from retroviruses, and mouse metallothionein-I. Selection of the appropriate vector and promoter and preparation of certain recombinant expression constructs comprising at least one promoter or regulated promoter operatively linked to a polynucleotide described herein is well within the level of ordinary skill in the art.

Useful bacterial expression constructs are prepared by inserting into an expression vector a structural DNA sequence encoding the desired peptide monomer together with suitable translation initiation and termination signals in an operative reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. Any other plasmid or vector may be used as long as the plasmid or vector is replicable and viable in the host.

T Cell Epitope Peptides and B Cell Epitope Peptides

The peptide monomers described herein optionally comprise at least one B cell or T cell epitope peptide linked (i.e., joined, conjugated) to the terminus of the amphipathic α-helical peptide. In certain embodiments, the peptide monomer comprises at least one T cell epitope peptide linked to the terminus of the amphipathic α-helical peptide. The at least one T cell epitope peptide may be linked to the N-terminus or to the C-terminus of the amphipathic α-helical peptide. In certain embodiments, at least two T cell epitope peptides are linked to the amphipathic α-helical peptide. The at least two T cell epitope peptides may be linked in series to the N-terminus or to the C-terminus of the amphipathic α-helical peptide. In other embodiments, a first T cell epitope peptide may be linked to the N-terminus, and a second T cell epitope peptide may be linked to the C-terminus of the amphipathic α-helical peptide. One skilled in the art will be able to readily determine the effect of linking an epitope peptide to the N- or C-terminus of the amphipathic α-helical peptide to ensure optimization of the ability of the amphipathic α-helical peptide to maintain the coiled-coil structure and/or to oligomerize.

In certain embodiments, a T cell epitope peptide is a $CD4^+$ T cell epitope. $CD4^+$ T cell epitopes are short peptide sequences about 9-22 amino acids in length that are presented by MHC Class II molecules to $CD4^+$ T cells (helper T cells) and evoke an immune response from the $CD4^+$ T cells. Inclusion of a $CD4^+$ T cell epitope peptide in the peptide monomer is useful for vaccine design because helper T cells are important for the development of memory B cells and high affinity antibody responses. In particular, inclusion of a $CD4^+$ T cell epitope peptide in the peptide monomer may be beneficial for enhancing the immune response specific for poorly immunogenic antigens such as haptens.

In certain embodiments, a T cell epitope peptide is a $CD8^+$ T cell epitope peptide. $CD8^+$ T cell epitopes are short peptide sequences about 8 to 11 amino acids in length that are presented by MHC Class I molecules to $CD8^+$ T cells and evoke an immune response from the $CD8^+$ T cells. Inclusion of a $CD8^+$ T cell epitope peptide in the peptide monomer is useful for stimulating a cytotoxic T cell response. Eliciting a cytotoxic T cells response is particularly useful for inducing an immune response to intracellular bacterial/viral infections and cancer.

A T cell receptor will recognize an epitope of a peptide antigen when it is bound to a host cell's MHC molecule (MHC-restricted antigen recognition). Major histocompatibility complex molecules (MHC molecules) are typically glycoproteins that deliver peptide antigens to a cell surface. MHC class I molecules are heterodimers consisting of a membrane spanning a chain (with three α domains) and a non-covalently associated β2 microglobulin. MHC class II molecules are composed of two transmembrane glycoproteins, α and β, both of which span the membrane. MHC class I molecules are expressed on all nucleated cells and deliver peptides originating in the cytosol to the cell surface, where the peptide:MHC complex is recognized by CD8+ T cells. MHC class II molecules are expressed by antigen presenting cells and deliver peptides originating in the vesicular system to the cell surface, where they are recognized by CD4+ T cells. MHC in humans may also be referred to as human leukocyte antigen (HLA).

In certain embodiments, the peptide monomer optionally comprises at least one B cell epitope peptide linked to the terminus of the amphipathic α-helical peptide. The at least one B cell epitope peptide may be linked to the N-terminus or to the C-terminus of the amphipathic α-helical peptide. In certain embodiments, at least two B cell epitope peptides are linked to the amphipathic α-helical peptide. The at least two B cell epitope peptides may be linked in series to the N-terminus or to the C-terminus of the amphipathic α-helical peptide. In other embodiments, a first B cell epitope peptide may be linked to the N-terminus, and a second B cell epitope peptide may be linked to the C-terminus of the amphipathic α-helical peptide.

Antibodies specifically bind to an antigen at portions of the antigen referred to as B-cell epitopes. A B cell epitope may be linear (i.e., a linear sequence of adjacent (contiguous) amino acids) or conformational (i.e., non-sequential amino acids or segments of the antigen that are brought together in spatial proximity when the corresponding antigen or a portion of the antigen is folded). A linear B cell epitope is a short peptide sequence, typically of between 5-20 contiguous amino acids in length.

In certain embodiments, the peptide monomer optionally comprises at least one B cell epitope peptide and at least one T cell epitope peptide linked to the amphipathic α-helical peptide. The at least one B cell epitope peptide and at least one T cell epitope peptide may be linked in series to the N-terminus or to the C-terminus of the amphipathic α-helical peptide. In other embodiments, a first B cell epitope peptide may be linked to the N-terminus, and a first T cell epitope peptide may be linked to the C-terminus of the amphipathic α-helical peptide, or vice versa.

In certain embodiments, rather than linking at least one B cell or T cell epitope peptide to a peptide monomer, an immunogenic composition comprising a peptide monomer, peptide dimer, or trimeric coiled coil peptide includes at least one B cell or T cell epitope peptide as an independent peptide to be administered concurrently to a subject. In certain embodiments, an immunogenic composition comprising a peptide monomer, peptide dimer, or trimeric coiled coil peptide includes one or more T cell epitope peptide(s).

A B cell or T cell epitope peptide may be selected from a variety of sources. An epitope peptide may be from a self-antigen or from a foreign antigen. In certain embodiments, a foreign antigen may be from a pathogenic microorganism. Pathogenic microorganisms include viral, bacteria, fungi, and protozoan species. In certain embodiments, a T cell epitope peptide is an influenza hemagglutinin T cell epitope peptide. In other certain embodiments, a T cell epitope peptide comprises an amino acid sequence of SEQ ID NO:6 (YQNPTTYISVK), SEQ ID NO:7 (SLEHPIVVSGSWD), SEQ ID NO:8 (ILMQYIKANSKFIGI), or SEQ ID NO:9 (QSIALSSLMVAQ). In certain embodiments, a self-antigen may be a cancer (i.e., tumor) antigen. In certain embodiments, an epitope peptide may be selected or designed to have a minimal number or no lysine or aspartic acid residues. Because the trimeric coiled-coil peptides are designed such that the haptens are conjugated to the solvent exposed lysine or aspartic acid residues, the presence of these residues in the epitope peptide may interfere with the ability of the epitope peptide to induce a strong T helper response. For example, a CD4+ T cell epitope peptide may be selected to have a minimal number or no lysine residues to avoid conjugation of a hapten to a lysine present in the epitope, thereby reducing or eliminating any interference with a strong CD4 memory T helper response.

A B cell or T cell epitope peptide may be selected using a variety of methods. An epitope may be determined by experimental methods known in the art, identified from the scientific literature, predicted using bioinformatics tools, designed de novo, or a combination of these methods. Methods for identifying antigenic epitopes have been previously described (see, for example, Sturniolo at al., *Nature Biotech.* 17: 555-61 (1999); Jameson et al., *Comput. Appl. Biosci.* 4:181-186 (1988); Nakai et al., *Trends Biochem. Sci.* 24:34-36 (1999); Hopp, *Pept. Res.* 6:183-90 (1993); Hofmann et al., *Biomed. Biochim. Acta* 46:855-66 (1987); Menendez et al., *Comput. Appl. Biosci.* 6:101-105 (1990). A number of publicly available databases exist that contain B cell and T cell epitopes (see, e.g., Lata et al., 2009, BMC Res. Notes 2:61; Bhasin et al., 2003, Bioinformatics 19:665-6; Immune Epitope Database and Analysis Resource (http://www.iedb.org/); Saha et al. 2005, BMC Genomics 6:79; Hans-Georg et al., 1999, *Immunogenetics* 50:213-219). Bioinformatic tools for epitope prediction are known in the art (see, e.g., Immune Epitope Database and Analysis Resource (see Internet site at iedb.org/); Sun et al., 2013, *Computational and Mathematical Methods in Medicine* vol. 2013, Article ID 943636; Singh et al., 2013, *PLos ONE* 8:e62216; Oyarzun et al., 2013, *BMC Bioinformatics* 14:52; Hoof et al., 2009, Immunogenetics 61:1-13; Wan et al., 2006, *BMC Bioinformatics* 7:463; Wang et al., 2010, *BMC Bioinformatics* 11:568).

In one example, a B cell or T cell epitope that is linked to or co-administered with the peptide carriers described herein may be a consensus or conserved epitope. A consensus or conserved epitope is highly conserved among multiple pathogenic microorganisms or among multiple subtypes or strains of a pathogenic microorganism.

In certain embodiments, a T cell epitope that is linked to or co-administered with the peptide carriers described herein may be a "promiscuous" or "universal" T cell epitope. A promiscuous or universal T-cell epitope means that it can be bound by multiple HLA alleles and stimulate antigen-specific T cells in association with the different HLA alleles. In a particular embodiment, a promiscuous T cell epitope is a CD4+ T cell epitope. In another particular embodiment, a promiscuous T cell epitope is a CD8+ T cell epitope. The utility of a defined T cell epitope is limited by its HLA restriction. Peptide epitopes usually form productive peptide-MHC complexes with a small number of HLA alleles and stimulate T cells responses only in individuals expressing those alleles. Therefore, promiscuous T-cell epitopes are useful components of immunotherapies because the epitopes may be useful for enhancing T helper responses in a wide patient population. A variety of promiscuous T-cell epitopes are known in the art, including for example, epitopes from pathogenic microorganisms, cancer antigens, allergens, or synthetic peptides. In certain embodiments, a promiscuous CD4+ T-cell epitope comprises an amino acid sequence of SEQ ID NO:6 or SEQ ID NO:9. In certain embodiments, a promiscuous T-cell epitope may be a pan DR epitope (PADRE) peptide. A PADRE peptide is a pan HLA DR-binding epitope peptide that promiscuously binds with high or intermediate affinity to multiple HLA-DR types. A PADRE peptide also cross-reacts with certain mouse class II alleles. PADRE peptides have been previously described (see, e.g., Alexander et al., 1994, *Immunity* 1:751; U.S. Pat. No. 5,736,142; La Rosa et al., 2012, *J. Infect. Dis.* 205: 1294-304; and U.S. Pat. No. 6,413,935). In certain embodiments, a T-cell epitope is a PADRE peptide comprising an amino acid sequence of SEQ ID NO:10 (AKFVAAWTL-KAAA). Bioinformatics tools for predicting peptide ligands with a broad range of HLA-binding specificity and databases of promiscuous epitopes are readily available see, e.g., (see, e.g., Bian and Hammer, 2004, *Method Bioinformatics in Vaccine Design* 34:468-475; Singh and Raghava, 2001, *Bioinformatics* 17:1236-7; Brusic et al., 2002, *Immunol. Cell Biol.* 80:280-5; Sturniolo et al., 1999, *Nat. Biotechnol.* 17:555-61).

In certain embodiments, a T cell epitope may be a restricted, customized, or personalized T cell epitope. It may be desirable to optimize clinical efficacy of a peptide carrier conjugate based vaccine described herein by appropriately matching the T cell epitope with an HLA type of particular group of subjects or an individual subject. By identifying the HLA alleles of the target population or target individual, a T cell epitope may be designed or selected to bind the identified HLA alleles and stimulate an antigen specific T cell response in the target population or target individual, thus creating a personalized vaccine.

In certain particular embodiments, the peptide monomer may comprise at least one protease site. A protease site that may be included in a peptide monomer is a site recognized by an intracellular protease located in a lysosomal/endosomal compartment of an antigen presenting cell. Most CD4+ T-cell responses are induced by proteins endocytosed from the extracellular milieu by specialized antigen-presenting cells (APCs) such as dendritic cells (DC). These proteins are then degraded in the acidic endosomal and lysosomal compartments, where they encounter MHC class II molecules. Their endocytosed epitopes are eventually presented at the cell surface. The three main classes of intracellular proteases residing in the lysosomal/endosomal compartments of antigen presenting cells and participating in antigen degradation are cysteine (cathepsin B, F, H, L, S, Z, and AEP, for asparaginyl endopeptidase), aspartate (cathepsin D, E), and serine (cathepsin A, G) proteases. The protease name indicates the amino acid of the protease active site for hydrolysis of the substrate peptide bond. Cathepsin cleavage sites have been well characterized (see, e.g., Lutzner and Kalbacher, 2008, *J. Biol. Chem.* 283:36185-36194; Biniossek et al., 2011, *J. Proteome Res.* 10:5363-73; Hewitt et al., 1997, *J. Immunol.* 159:4693-4699). Examples of protease cleavage sites include the cathepsin S cleavage site PMGLP (SEQ ID NO: 11) and an non-specific cathepsin cleavage site KVSVR (SEQ ID NO: 12).

Inclusion of proteolytic cleavage sites adjacent to a T cell epitope that is linked to a peptide monomer provides a site for intracellular proteases to separate the epitope from the peptide carrier after internalization by the antigen presenting cell. Consequently, presentation of the T cell epitope may be improved when the peptide is taken up by the antigen presenting cell. Inclusion of proteolytic cleavage sites adjacent to T cell epitopes in vaccine design is known in the art (see, e.g., Smahel, 2014, *Gene Therapy* 21:225-232; Verma et al., 1995, *Vaccine* 13:235-44; Fraser et al., 2014, Vaccine 32:2896-903). In certain embodiments, a proteolytic cleavage site comprises an amino acid sequence of SEQ ID NO:11 (PMGLP) or SEQ ID NO:12 (KVSVR).

In certain embodiments, a peptide monomer is linked to at least one T-cell epitope peptide and includes an internal proteolytic cleavage site between the amphipathic α-helical peptide and at least one T-cell epitope peptide. In certain embodiments when two or more T-cell epitopes are arranged in series in a peptide monomer, an internal proteolytic cleavage site may be present between the amphipathic α-helical peptide and the T-cell epitope peptide linked to the helical peptide's terminus and also between each T-cell epitope. When two or more proteolytic cleavage sites are incorporated into a peptide monomer, each cleavage site may the same. In other embodiments, when two or more proteolytic cleavage sites are incorporated into a peptide monomer, each cleavage site may different such that each different site is recognized and cleaved by different proteases.

Polymeric Coiled-Coil Peptides

In certain embodiments, the disclosure provides a peptide dimer comprising two peptide monomers according to any of the embodiments described herein. The two peptide monomers, each comprising an amphipathic α-helical peptide, may assemble to form a stable, parallel bundle of α-helical peptides in aqueous solution. Following assembly, the charged lysines, aspartic acid, or glutamic acid residues are solvent-exposed on the helix surface for hapten conjugation, and the repeating isoleucine residues form a hydrophobic core along the length of the peptide dimer. Arginine and glutamic acid residues within the repeating heptad are strategically placed to form salt bridges between adjacent helices to further stabilize the dimeric structure. The amphipathic α-helices of the peptide monomers oligomerize through their hydrophobic surfaces. In certain embodiments, the peptide monomers for assembling into a peptide dimer have identical amino acid sequences (homodimer). For example, identical peptide monomers have the same amphipathic α-helical peptide sequence, same epitope peptide sequence (if linked to the peptide monomer rather than administered separately), and same optional proteolytic cleavage site peptide sequence. Peptide monomers comprising identical or substantially identical sequences preserve the desirable structure, stability, dimeric oligomerization state, and high density of solvent exposed residues for hapten conjugation to the peptide dimer. In certain embodiments, the peptide monomers making up a peptide dimer have the same amphipathic α-helical peptide sequence but different epitope peptide sequences. When proteolytic cleavage sites are included in the peptide monomer, the proteolytic cleavage site peptides may be the same or different.

In certain embodiments, the present disclosure provides a peptide dimer conjugate comprising a peptide dimer linked to a hapten. In certain embodiments, the peptide dimer is linked to at least two haptens. In certain embodiments, the peptide dimer is linked to at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 110, 120, 130, or 140 hapten molecules, which hapten molecules may be the same or different. The hapten molecules are linked to lysine or aspartic acid residues of the peptide monomer before or after dimerization of the peptide monomers.

In certain embodiments, a dimeric coiled-coil peptide conjugate contains an average of 0.6, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hapten molecules per peptide monomer, which hapten molecules may be the same or different. The maximum potential number of hapten molecules that may be conjugated to a peptide dimer depends upon the number of lysine or aspartic acid residues available, which are in turn determined by the number of heptad repeats in each peptide monomer. For example, a peptide monomer comprising an amino acid sequence of SEQ ID NO:1 or SEQ ID NO:3 has 16 lysine or aspartic acid residues, respectively, for conjugation with a hapten. Thus, a peptide dimer comprising two peptide monomers (each of the two peptide monomers comprises SEQ ID NO:1 or SEQ ID NO:3) has a total of 32 lysine or aspartic acid residues, respectively, available for conjugation with a hapten. For a peptide monomer comprising an amphipathic α-helical peptide amino acid sequence according to the formula (E or X)XIEXR-[I(E or X)XIEXR]$_n$-I(E or X)X, wherein X=K for each instance, or each X is independently selected from D and E, and n=any integer between and including 1-20; there are potentially up to 3n+5 lysine or aspartic acid residues available for conjugation with a hapten. A peptide dimer comprising identical peptide monomer sequences would have 2(3n+5) lysine or aspartic acid residues available for conjugation with a hapten.

In certain embodiments, the disclosure provides a trimeric coiled-coil peptide comprising a trimer of the peptide monomers according to any of the embodiments described herein. The three peptide monomers, each comprising an amphipathic α-helical peptide, spontaneously assemble to form a stable, parallel bundle of α-helical peptides in aqueous solution (i.e., trimeric coiled-coil). Following assembly, the charged lysines, aspartic acid, or glutamic acid residues are solvent-exposed on the helix surface for hapten conjugation, and the repeating isoleucine residues form a hydrophobic core along the length of the trimeric coiled-coil that permit oligomerization with other helices. Arginine and glutamic acid residues within the repeating heptad are strategically placed to form salt bridges between adjacent helices to further stabilize the trimeric structure. The amphipathic α-helices of the peptide monomers oligomerize through their hydrophobic surfaces. In certain embodiments, the peptide monomers for assembling into a trimeric coiled-coil peptide have identical amino acid sequences (homotrimer). For example, identical peptide monomers have the same amphipathic α-helical peptide sequence, same epitope peptide sequence (if linked to the peptide monomer rather than administered separately), and same optional proteolytic cleavage site peptide sequence. Peptide monomers comprising identical or substantially identical sequences preserve the desirable structure, stability, trimeric oligomerization state, and high density of solvent exposed residues for hapten conjugation of the trimeric coiled-coil. In certain embodiments, the peptide monomers making up a trimeric coiled-coil peptide have the same amphipathic α-helical peptide sequence but different epitope peptide sequences. When proteolytic cleavage sites are included in the peptide monomer, the proteolytic cleavage site peptides may be the same or different.

In certain embodiments, the present disclosure provides a trimeric coiled-coil peptide conjugate comprising a trimeric coiled-coil peptide linked to a hapten. In certain embodiments, the trimeric coiled-coil peptide is linked to at least two haptens. In certain embodiments, the trimeric coiled-coil peptide is linked to at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 110, 120, 130, or 140 hapten molecules, which hapten molecules may be the same or different. The hapten molecules are linked to lysine or aspartic acid residues of the peptide monomer before or oligomerization into a trimeric coiled-coil peptide.

In certain embodiments, a trimeric coiled-coil peptide conjugate contains an average of 0.6, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hapten molecules per peptide monomer, which hapten molecules may be the same or different. The maximum potential number of hapten molecules that may be conjugated to a trimeric coiled-coil peptide depends upon the number of lysine or aspartic acid residues available, which are in turn determined by the number of heptad repeats in each peptide monomer. For example, a peptide monomer comprising an amino acid sequence of SEQ ID NO:1 or SEQ ID NO:3 has 16 lysine or aspartic acid residues, respectively, for conjugation with a hapten. Thus, a trimeric coiled-coil peptide comprising three peptide monomers (each of which three peptide monomers comprises SEQ ID NO:1 or SEQ ID NO:3) has a total of 48 lysine or aspartic acid residues, respectively, available for conjugation with a hapten. For a peptide monomer comprising an amphipathic α-helical peptide amino acid sequence according to the formula (E or X)XIEXR-[I(E or X)XIEXR]$_n$-I(E or X)X, wherein X=K for each instance, or each X is independently selected from D and E, and n=any integer between and including 1-20; there are potentially up to 3n+5 lysine or aspartic acid residues available for conjugation with a hapten. A trimeric coiled-coil peptide comprising identical peptide monomer sequences would have 3(3n+5) lysine or aspartic acid residues available for conjugation with a hapten.

In certain embodiments, the present disclosure provides a peptide monomer conjugated to a hapten. In certain embodiments, the peptide monomer is linked to at least two haptens. In certain embodiments, the peptide monomer is linked to at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 110, 120, 130, or 140 hapten molecules, which hapten molecules may be the same or different.

In certain embodiments, a peptide monomer conjugate contains an average of 0.6, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hapten molecules, which hapten molecules may be the same or different. The maximum potential number of hapten molecules that may be conjugated to a peptide monomer depends upon the number of lysine or aspartic acid residues available, which are in turn determined by the number of heptad repeats in a peptide monomer. For example, a peptide monomer comprising an amino acid sequence of SEQ ID NO:1 or SEQ ID NO:3 has 16 lysine or aspartic acid residues, respectively, for conjugation with a hapten. For a peptide monomer comprising an amphipathic α-helical peptide amino acid sequence according to the formula (E or X)XIEXR-[I(E or X)XIEXR]$_n$-I(E or X)X, wherein X=K for each instance, or each X is independently selected from D and E, and n=any integer between and including 1-20; there are potentially up to 3n+5 lysine or aspartic acid residues available for conjugation with a hapten.

A person skilled in the art will appreciate that in a conjugation reaction, not every available lysine or aspartic acid residue may be coupled to a hapten. Chemical coupling of the peptide carrier to a hapten leads to a statistical mixture of various peptide carrier-hapten products. In other words, such conjugates comprise a statistical mixture of many different coupling products, i.e., peptide carriers that do not comprise a hapten conjugated to the peptide, peptide carriers comprising one hapten conjugated thereto, peptide carriers comprising two haptens conjugated thereto, peptide carriers comprising three haptens conjugated thereto, and so on. Each of these peptide carrier-hapten product subgroups is characterized by a uniform stoichiometry. This means that, e.g., the subgroup comprising one hapten per peptide carrier has a uniform stoichiometry of 1:1. The peptide carrier conjugates described herein have an advantage of uniform exposure of the hapten to the solvent, high hapten density, and hapten periodicity.

In certain embodiments when a monomeric peptide, dimeric peptide, or trimeric coiled coil peptide is linked to multiple haptens, each hapten may be the same (identical) molecular moiety. In other embodiments when a monomeric peptide, dimeric peptide, or trimeric coiled-coil peptide is linked to multiple haptens, the multiple haptens may be selected from 2, 3, 4, 5, 6, 7, 8, 9, or 10 non-identical hapten molecules. The non-identical haptens may be selected from the same type of hapten (e.g., a specific small molecule and at least one analog thereof) or may be selected from different types of haptens (e.g., different small molecules, or a carbohydrate and a peptide, or different carbohydrates, or different peptides). By way of example, non-identical haptens may be representative of the same drug of abuse (e.g., nicotine). In another example, non-identical haptens may represent different drugs of abuse (e.g., nicotine and cocaine). In yet another example, when a peptide carrier is linked to multiple non-identical haptens, the multiple non-identical haptens may be selected from nicotine, nicotine analogs, and structurally distinct nicotine haptens. Recent studies have shown that co-immunization of structurally distinct nicotine haptens produced additive antibody responses (see, de Villiers et al., 2013, Vaccine 31:6185-6193; Keyler et al., 2008, Int. Immunopharmacol. 8:1589-1594). A multivalent vaccine based on the peptide carriers described herein could activate numerous B cell populations and augment functional antibody responses even further. In another example, when a peptide carrier is linked to multiple non-identical haptens, the multiple non-identical haptens may be selected from different types of haptens, such as i) nicotine, nicotine analogs, and structurally distinct nicotine haptens, and ii) cocaine, cocaine analogs, and structurally distinct cocaine haptens.

Haptens

The monomeric, dimeric, and trimeric peptides described herein are useful hapten (i.e., antigenic) carrier molecules for vaccines (i.e., immunogenic compositions). Small molecules that are not good immunogens but become more immunogenic when attached to a larger molecule are called haptens. A hapten may be a small organic molecule, a monosaccharide, disaccharide, or oligosaccharide, a lipid, nucleic acid, or an oligopeptide, for example. Although a hapten may be capable of binding to an antibody, immunization with a hapten does not usually provoke an antibody response. As described herein, immunogenicity may be achieved by covalently attaching (i.e., linking, joining, conjugating) a hapten to a larger molecule, called the carrier. Databases that describe thousands of haptens are available in the art (see, e.g., Gunther et al., 2007, Nucl. Acids Res. 35:D906-D910; Singh et al., 2006, Bioinformatics 2006, 22:253-255).

In certain embodiments, a peptide monomer conjugate comprises a peptide monomer linked to a hapten, wherein the hapten is linked to a lysine or aspartic acid residue of the peptide monomer. In certain embodiments, a peptide monomer conjugate comprises a peptide monomer linked to at least two haptens. In certain embodiments, a peptide dimer conjugate comprises a peptide dimer linked to a hapten, wherein the hapten is linked to a lysine or aspartic acid residue of a peptide monomer making up the peptide dimer. In certain embodiments, a peptide dimer conjugate comprises a peptide dimer linked to at least two haptens. In certain embodiments, a trimeric coiled-coil peptide conjugate comprises a trimeric coiled-coil peptide linked to a hapten, wherein the hapten is linked to a lysine or aspartic acid residue of the peptide monomer. In certain embodiments, a trimeric coiled-coil peptide conjugate comprises a trimeric coiled-coil peptide linked to at least two haptens. In one embodiment, a hapten is a small organic molecule.

In a specific embodiment, a hapten is a drug of abuse, for example, nicotine, ethyl alcohol, opiates, cannabinoids, amphetamines, barbiturates, glutethimide, methyprylon, chloral hydrate, methaqualone, benzodiazepines, LSD, anticholinergic drugs, antipsychotic drugs, tryptarine, other psychomirnetic drugs, sedatives, tranquilizers, cough suppressants, hallucinogens, stimulants, phencyclidine, psilocybine, volatile nitrite, benzodiazepine, other drugs inducing physical dependence and/or psychological dependence, or analogs of each of the drugs.

In a more specific embodiment, a hapten is nicotine, a stereoisomer thereof, an analog thereof, or a structurally distinct nicotine hapten. Nicotine is parasympathomimetic alkaloid found in Solanaceae plants (e.g. tobacco) that acts as a potent stimulant. Nicotine is also known as (S)-3-[1-Methylpyrrolidin-2-yl]pyridine. Such analogs are known in the art. Nicotine analogs and formulations are described in U.S. Pat. Nos. 5,776,957; 4,965,074; 5,278,176; 5,276,043; 5,227,391; 5,214,060; 5,242,934; 5,223,497; 5,278,045; 5,232,933; 5,138,062; 4,966,916; 4,442,292; 4,321,387; 5,069,094; 5,721,257, all of which are incorporated herein by reference. Analogs include, for example, nicotine wherein the N-methyl group has been replaced with a higher order alkyl group.

In another example, analogs include nicotine molecules that comprise a moiety attached at the 5- or 6-position of the pyridine ring via an ether linkage.

Accordingly, an analog of nicotine may have the following structure of formula (I):

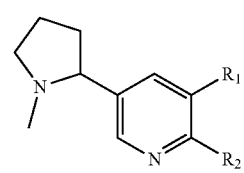

or a single stereoisomer, a mixture of stereoisomers, tautomer or pharmaceutically acceptable salt thereof, wherein one of $R_1$ and $R_2$ is —(CH$_2$)$_m$C(=O)(OH), —(CH$_2$)$_m$C(=O)O-L, —O—(CH$_2$)$_n$—NH$_2$, —O—(CH$_2$)—NH-L, —O—(CH$_2$)$_n$C(=O)OH, or —O—(CH$_2$)$_n$C(=O)O-L, and the other of R$_1$ and R$_2$ is hydrogen, and wherein m is 2-20 and n is 1, 2, or 3. In certain embodiments, n is 1. In other embodiments, m is 2-10 or 3-8. In other specific embodiments, m is 4, 5, or 6. In a more specific embodiment, m is 5. An example of a compound of formula (I), wherein R$_1$ is H and R$_2$ is —(CH$_2$)$_m$C(=O)(OH) wherein m is 5, is nicotine 6-hexanoic acid (see FIG. 1A). In another specific embodiment, R$_2$ is H and R$_1$ is —(CH$_2$)$_m$C(=O)(OH) wherein m is 5. Other examples include compounds wherein R$_1$ is —O—CH$_2$—NH$_2$ or —O—CH$_2$C(=O)OH and R$_2$ is H. In still other embodiments, R$_2$ is —O—CH$_2$—NH$_2$ or —O—CH$_2$C(=O)OH and R$_1$ is H. (See, for example, H1-H4 in FIG. 13.) In certain embodiments, whichever of R$_1$ and R$_2$ is not hydrogen, the substituent may further comprise a linker moiety. L is a linker having a structure that is known in the art that can be used to attach a small organic molecule to an amino acid residue of a peptide or polypeptide.

Examples of nicotine haptens that are structurally distinct from each other include, for example, nicotine, 6-(carboxymethylureido)-(±)-nicotine (6-CMUNic), trans-3'-aminomethyl-(±)-nicotine (3'-AmNic), and 1'-N-(2-mercaptoethyl) pentanamide-(-)-nicotine (1'-SNic).

Any suitable linker can be used in accordance with the present disclosure. Linkers may be used to form amide linkages, ester linkages, disulfide linkages, etc. Linkers may contain carbon atoms or heteroatoms (e.g., nitrogen, oxygen, sulfur, etc.). Typically, linkers are 1 to 50 atoms long, 1 to 40 atoms long, 1 to atoms long, 1 to 20 atoms long, 1 to 15 atoms long, 1 to 10 atoms long, or 1 to 10 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in the art, each of these groups may in turn be substituted.

In some embodiments, a linker is an aliphatic or heteroaliphatic linker. In some embodiments, the linker is a polyalkyl linker. In certain embodiments, the linker is a polyether linker. In certain embodiments, the linker is a polyethylene linker. In certain specific embodiments, the linker is a polyethylene glycol (PEG) linker.

In more specific embodiments, a linker may comprise an amino group or carboxyl group at the terminal end to which a structure of formula (I) may be attached. In particular embodiments, the linker L is HO—C(=O)(CH$_2$)p-C(=O)—O-Q or NH$_2$(CH$_2$)pC(=O)—O-Q wherein Q is a protecting group and wherein p is any integer between and including 1-8. In certain embodiments, p is 2, 3, 4, 5, 6, or 7. In other embodiments, the linker L comprises a PEG moiety, for example, the linker may be NH$_2$(CH$_2$—CH$_2$—O)$_y$(CH$_2$)$_z$C(=O)—O-Q or HO—C(=O)(CH$_2$—CH$_2$—O)$_y$(CH$_2$)$_z$C(=O)—O-Q wherein y is any integer between and including 2-10 and z is 1, 2, or 3. In certain embodiments, y is 2, 3, 4, or 5. In other certain embodiments, z is 2. Examples of linker moieties are illustrated in FIG. 13 (see L1, L2, L3, and L4).

Figure 13:
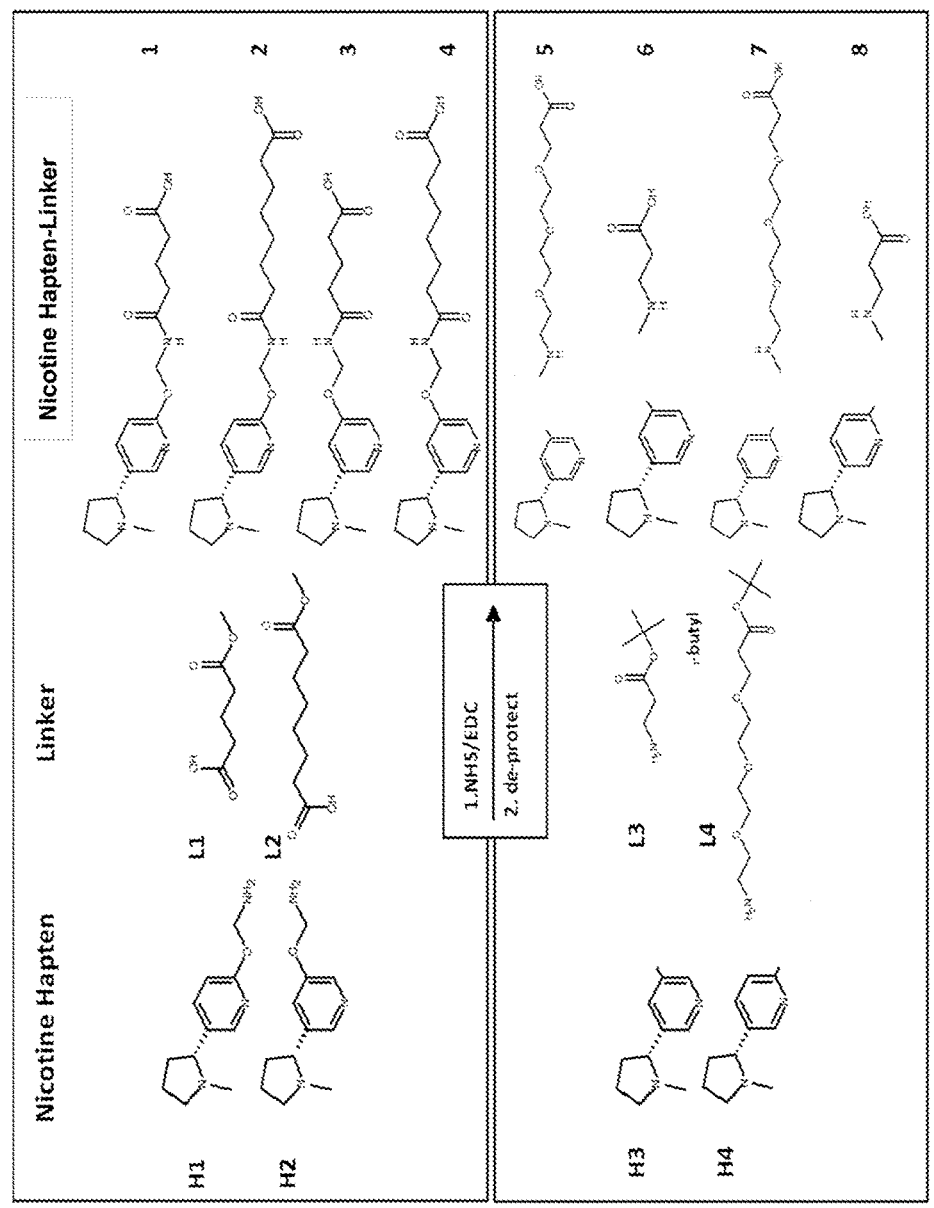
FIG. 13 shows exemplary structures of nicotine haptens, linkers, combined nicotine hapten linkers, with varying attachment sites on the pyridine ring and linker lengths. Amino or carboxyl groups are added to nicotine via an ether linkage at the 5- or 6-position of the pyridine ring to yield haptens H1-H4. Haptens H1 and H2 have an amino group attached to the 6- and 5-position of the pyridine ring, respectively. Haptens H3 and H4 have a carboxyl group attached to the 5- and 6-position of the pyridine ring, respectively. Exemplary nicotine hapten-linker structures 1 (H1-L1), 2 (H1-L2), 3 (H2-L1), 4 (H2-L2), 5 (H3-L4), 6 (H3-L3), 7 (H4-L4), and 8 (H4-L3) are shown.

In still more specific embodiments, a nicotine hapten is the nicotine analog, nicotine 6-hexanoic acid, H1 hapten, H2 hapten, H3 hapten, or H4 hapten (see H1, H2, H3, and H4 in FIG. 13, left column). In other specific embodiments, the nicotine analog comprises a linker moiety such that the analog has a structure of any one of the nicotine hapten-linker structures 1-8 shown in FIG. 13 (far right column).

In another specific embodiment, a peptide carrier is linked to at least two haptens, wherein the at least two haptens are selected from nicotine, nicotine analogs, and structurally distinct nicotine haptens.

Nicotine hapten as described herein may be a nicotine salt. The nicotine salt or nicotine analog salt described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of compounds of structures (I) as well as any and all substructures and specific compounds described herein is intended to encompass any and all pharmaceutically suitable salt forms. Accordingly, the nicotine salt or nicotine analog salt may be a salt that contains pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts.

In certain embodiments, a nicotine hapten may comprise a nicotine derivative. Derivatives of nicotine include conjugates of nicotine covalently bonded to another species (such as a polymer, oligomer, or small molecule). A number of useful derivatives of nicotine are disclosed within the Physician's Desk Reference as well as Harrison's Principles of Internal Medicine.

With regard to stereoisomers, the nicotine compounds of structure (I), as well as any substructure or structures described herein, may have one or more chiral (or asymmetric) centers, and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans). Likewise, unless otherwise specified, all possible isomers, as well as their racemic and optically pure forms, and all tautomeric forms are also intended to be included. It is therefore contemplated that various stereoisomers and mixtures thereof and includes "enantiomers," which refers to two stereoisomers whose molecules are non-superimposeable mirror images of one another. Thus, the compounds may occur in any isomeric form, including racemates, racemic mixtures, and as individual enantiomers or diastereomers. A "tautomer" refers to a proton shift from one atom of a molecule to another atom of the same molecule. Some embodiments of the disclosed compounds include tautomers of any said compounds.

In another specific embodiment, a hapten is a carbohydrate, such as a carbohydrate of a pathogenic microorganism or a carbohydrate from a self-antigen, such as a tumor antigen. In some embodiments, the carbohydrate hapten is derived from a pathogenic microorganism (bacteria, virus, fungus, protozoan, parasite). Carbohydrates associated with pathogenic microorganisms can be expressed on their surface, secreted, shed, or on the surface of infected host cells. Carbohydrate haptens from a pathogenic microorganism may be from capsules composed of polysaccharides, lipopolysaccharides, exopolysaccharides (e.g., polysaccharides that form a biofilm), 0-linked polysaccharides (or portions thereof), mannan (*Candida albicans*), lipophosphoglycan (*Leishmania major*), or viral glycoproteins. In other embodiments, a carbohydrate hapten is derived from a self-antigen, for example a tumor antigen. Examples of carbohydrate haptens from a tumor include, for example, glycosphingolipids, mucin-type carbohydrates, lactosylceramid, $Le^x$, $Le^y$, GD3, GD2, Globo-H, GB3, and Tn antigen.

In another specific embodiment, a hapten is a toxin. A toxin may be derived from a pathogenic microorganism, a venomous organism, or a chemical weapon. Examples of toxins include for example, botulinum toxin, phosphine, O-Alkyl (<C10, incl. cycloalkyl) alkyl (Me, Et, n-Pr or i-Pr)-phosphonofluoridates (e.g., Sarin: O-Isopropyl methylphosphonofluoridate, Soman: O-Pinacolyl methylphosphonofluoridate), O-Alkyl (<C10, incl. cycloalkyl) N,N-dialkyl (Me, Et, n-Pr or i-Pr) phosphoramidocyanidates (e.g., Tabun: O-Ethyl N,N-dimethylphosphoramidocyanidate), O-Alkyl (H or <C10, incl. cycloalkyl)S-2-dialkyl (Me, Et, n-Pr or i-Pr)-aminoethyl alkyl (Me, Et, n-Pr or i-Pr) phosphonothiolates and corresponding alkylated or protonated salts (e.g., VX: O-Ethyl S-2-diisopropylaminoethyl methylphosphonothiolate), Sulfur mustards (2-Chloroethylchloromethylsulfide), Mustard gas (Bis(2-chloroethyl)sulfide), Bis(2-chloroethylthio)methane, Sesquimustard (1,2-Bis(2-chloroethylthio)ethane), 1,3-Bis(2-chloroethylthio)-n-propane, 1,4-Bis(2-chloroethylthio)-n-butane, 1,5-Bis(2-chloroethylthio)-n-pentane, Bis(2-chloroethylthiomethyl) ether, O-Mustard (Bis(2-chloroethylthioethyl)ether), Lewisites (Lewisite 1 (2-Chlorovinyldichloroarsine), Lewisite 2 (Bis(2-chlorovinyl)chloroarsine), Lewisite 3 (Tris(2-chlorovinyl)arsine)), Nitrogen mustards (FIN1 (Bis (2-chloroethyl)ethylamine), HN2 (Bis(2-chloroethyl)methylamine), HN3 (Tris(2-chloroethyl)amine)), Saxitoxin, Ricin, Amiton (O,O-Diethyl S-(2-(diethylamino)ethyl)phosphorothiolate and corresponding alkylated or protonated salts), PFIB (1,1,3,3,3-Pentafluoro-2-(trifluoromethyl)-1-propene), 3-Quinuclidinyl benzilate (BZ), Phosgene (Carbonyl dichloride), Cyanogen chloride, Hydrogen cyanide, and Chloropicrin (Trichloronitromethane).

In another specific embodiment, a hapten is a hazardous environmental agent. Exemplary hazardous environmental agents include arsenic, lead, mercury, vinyl chloride, polychlorinated biphenyls, benzene, polycyclic aromatic hydrocarbons, cadmium, benzo(a)pyrene, benzo(b)fluoranthene, chloroform, dichlor-diphenyl-trichlorethylene (DDT), P,P'-, aroclor 1254, aroclor 1260, dibenzo(a,h)anthracene, trichloroethylene, dieldrin, chromium hexavalent, or p,p'-dichlorodiphenyldichloroethene (DDE, P,P').

In yet another specific embodiment, a hapten is a peptide. A hapten peptide may be a foreign antigen, for example, a peptide from a pathogenic microorganism, or a self-antigen. A self-antigen may be a cancer antigenatopic disease antigen, autoimmune disease antigen, alloantigen, xenoantigen, metabolic disease enzyme or enzymatic product. The use of self-antigens or a pathogenic microorganism antigens in cancer or infectious disease peptide vaccine development is well known in the art (see, e.g., Weidermann et al., 2013, *Breast Cancer Res. Treat* 138:1-12; Aranda et al., 2013, *OncoImmunology* 2:e26621; Yamada et al., 2013, *Cancer Sci.* 104:15-21; Hecht et al., 2009, *Curr. Opin. Chem. Biol.* 13:354-359; Vigneron et al., 2013, *Cancer Immunity* 13:15; Dalziel et al., 2014, *Science* 343, 1235681, DOI: 10.1126/science.1235681).

Physical association of the hapten and the peptide carrier described herein can be achieved in a variety of different ways. Physical association may be covalent or non-covalent. The peptide carrier and hapten may be directly associated with one another, e.g., by one or more covalent bonds, or may be associated by means of one or more linkers. In one embodiment, a linker forms one or more covalent or non-covalent bonds with the peptide carrier and one or more covalent or non-covalent bonds with the hapten, thereby attaching them to one another. In some embodiments, a first linker forms a covalent or non-covalent bond with the peptide carrier, and a second linker forms a covalent or non-covalent bond with the hapten. The two linkers form one or more covalent or non-covalent bond(s) with each other.

Any suitable linker can be used in accordance with the present disclosure. Linkers may be used to form amide linkages, ester linkages, disulfide linkages, etc. Linkers may contain carbon atoms or heteroatoms (e.g., nitrogen, oxygen, sulfur, etc.). Typically, linkers are 1 to 50 atoms long, 1 to 40 atoms long, 1 to 25 atoms long, 1 to 20 atoms long, 1 to 15 atoms long, 1 to 10 atoms long, 3-15 atoms long, or 3 to 10 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in the art, each of these groups may in turn be substituted.

In some embodiments, a linker is an aliphatic or heteroaliphatic linker. In some embodiments, the linker is a polyalkyl linker. In certain embodiments, the linker is a polyether linker. In certain embodiments, the linker is a polyethylene linker. In certain specific embodiments, the linker is a polyethylene glycol (PEG) linker. More specific embodiments of linker moieties that may be used with a hapten, such as nicotine or an analog thereof, are described in greater detail herein.

In some embodiments, the linker is a cleavable linker. Cleavable linkers include, for example, protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g. esterase cleavable linker), ultrasound-sensitive linkers, x-ray cleavable linkers, etc. In some embodiments, the linker is not a cleavable linker.

Any of a variety of methods can be used to associate a linker with a peptide carrier. General strategies include passive adsorption (e.g., via electrostatic interactions), multivalent chelation, high affinity non-covalent binding between members of a specific binding pair, covalent bond formation, etc. (see, e.g., Gao et al., 2005, *Curr. Op. Bio-* technol., 16:63; incorporated herein by reference). In some embodiments, click chemistry can be used to associate a linker with a peptide carrier.

A bi-functional cross-linking reagent may be used to attach a hapten to a peptide carrier. Such reagents contain two reactive groups, thereby providing a means of covalently associating two target groups. The reactive groups in a chemical cross-linking reagent typically belong to various classes of functional groups such as succinimidyl esters, maleimides, and pyridyldisulfides. Exemplary cross-linking agents include, e.g., carbodiimides, N-hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), N-Succinimidyl 3-[2-pyridyldithio]-propionamido (SPDP), succimidyl α-methylbutanoate, biotinamidohexanoyl-6-amino-hexanoic acid N-hydroxy-succinimide ester (SMCC), succinimidyl-[(N-maleimidopropionamido)-dodecaethyleneglycol]ester (NHS-PEO12), etc. For example, carbodiimide-mediated amide formation and active ester maleimide-mediated amine and sulfhydryl coupling are commonly used approaches.

A hapten may be attached to the peptide carrier (i.e., peptide monomer, peptide dimer, or trimeric coiled-coil peptide) with or without a linker. In certain embodiments, a hapten will contain a reactive functional group to which the peptide carrier can be attached directly, or via a linker. In a specific embodiment, a hapten is attached to the peptide carrier via an amide or disulfide bond. General methods for directly conjugating haptens to carrier proteins using a homobifunctional or heterobifunctional cross-linker are known in the art (see, e.g., Hermanson in *Bioconjugate Techniques*, Academic Press (1996); Dick and Beurret in *Conjugate Vaccines, Contribu. Microl. Immunol.* Karger, Basal (1989) 10:48-114). When using direct conjugation with bi-functional crosslinkers, the molar ratio of hapten to carrier is limited by the number of functional groups available on the carrier for the specific conjugation chemistry. By way of example, with a trimeric coiled-coil peptide having n number of lysine residues, there are "n" primary amines available for reaction with the bi-functional linker's carboxylic group. Thus, the trimeric coiled-coil product will be limited to having n amide bonds formed and a maximum of n haptens attached. The actual ratio of hapten to trimeric coiled-coil peptide may vary depending on various factors such as the concentration of reactants in the conjugation reaction and the nature of the trimeric coiled-coil peptide. In certain instances, a hapten may attach to non-amine moieties, such as —SH and —OH. However, these reactions typically occur with low frequency. Stable hapten-peptide carrier linkages are desired to prolong the shelf life of the vaccine.

In certain embodiments, a hapten is linked to the peptide carrier using a water soluble carbodiimide crosslinker. EDC is an example of a water-soluble carbodiimide crosslinker that activates carboxyl groups for spontaneous reaction with primary amines, enabling peptide immobilization and hapten-carrier protein conjugation. 1-Ethyl-3-[3-dimethylaminopropyl]carbodiimide hydrochloride (EDC or EDAC) is a zero-length crosslinking agent used to couple carboxyl groups to primary amines. EDC reacts with a carboxyl to form an amine-reactive O-acylisourea intermediate. If this intermediate does not encounter an amine, it will hydrolyze and regenerate the carboxyl group. In certain embodiments, EDC conjugation reaction may include Sulfo-NHS (N-hydroxysulfosuccinimide) reagent or its uncharged analog NHS (N-hydroxysuccinimide) to increase reaction efficiency or to stabilize active O-acylisourea intermediate for later reaction to amines. In the presence of NHS or Sulfo-NHS, EDC can be used to convert carboxyl groups to stable amine-reactive NHS esters or Sulfo-NHS esters. In a specific embodiment, a hapten is linked to a peptide carrier using EDC and NHS conjugation reaction.

The immunogenicity and function of nicotine-conjugate antigens may be influenced by the nicotine hapten (or nicotine analogs, structurally distinct nicotine haptens), the nature of the linker, and its site of attachment to nicotine. A common site of linker attachment to nicotine, which has been used in three clinical-stage vaccines, involves conjugation via the 3'-position on the 5 atom pyrrolidine ring (see, e.g., Pentel and LeSage, 2014, *Adv. Pharmacol.* 69:553-80). A recent study suggests that an intact and unhindered pyrrolidine ring is desired for good functional antibody responses, as improved responses were observed with linker attachments at the 5-, 6-, or 2-positions of the pyridine ring as compared to nicotine haptens with pyrrolidine substitutions or linker attachments (see, e.g., Pryde et al., 2013, PLoS One 8:e76557). Without wishing to be bound by theory, another site for linker attachment is the pyridine ring since it might increase the specificity for antibodies for nicotine rather than its metabolites like cotinine (see, e.g., de Villiers et al., 2010, *Vaccine*, 228:2161-8; Pryde et al., 2013, *PLoS One* 8:e76557). A rigid, conformationally constrained nicotine may be used as hapten, which presents a "fixed" epitope to limit rotation about the bond between its pyridine and pyrrolidine rings (see, e.g., Moreno and Janda, 2009, *Pharmacology, Biochemistry, and Behavior* 92:199-205). By tethering a nicotine analog to its carrier, the linker provides the geometry of the hapten epitope for antigen presentation and B cell activation. The length of the linker and the chemical properties of the linker (e.g., lipophilicity, hydrophilicity) may vary depending on the particular hapten and particular desired immune response.

Pharmaceutically Acceptable Immunogenic Compositions

Also provided herein are pharmaceutically acceptable immunogenic compositions (i.e., vaccines) comprising an immunogen (i.e., any of the peptide monomer conjugates, peptide dimer conjugates, or trimeric coiled-coil peptide conjugates described herein) and a pharmaceutically acceptable excipient. An immunogen is an antigen that is able to evoke an immune response, including production of antibodies via the humoral response. An antigen is any substance that may be specifically bound by components of the immune system (e.g., antibody, lymphocytes). Although all antigens are recognized by specific lymphocytes or by antibodies, not every antigen can evoke an immune response. Those antigens that are capable of inducing an immune response are said to be immunogenic and are called immunogens. The immunogenic composition may be a sterile aqueous or non-aqueous solution, suspension or emulsion, which additionally comprises a pharmaceutically acceptable carrier (physiologically acceptable excipient or pharmaceutically suitable excipient or carrier) (i.e., a non-toxic material that does not interfere with the activity of the active ingredient). An effective amount or therapeutically effective amount refers to an amount of the immunogen administered to a subject, either as a single dose or as part of a series of doses, which is effective to produce a desired therapeutic effect.

In certain embodiments, an immunogenic composition comprises a peptide monomer conjugate, a peptide dimer conjugate, or a trimeric coiled-coil peptide conjugate and at least one T-cell epitope peptide. For those peptide carriers that are not linked to a T cell epitope peptide, at least one T cell epitope peptide is administered concurrently with the peptide carrier conjugate. The T cell epitope peptide may be in the same immunogenic composition as the peptide carrier conjugate as a single vaccine formulation. Alternatively, the T cell epitope peptide may be in a separate formulation from the peptide carrier conjugate and administered concurrently (or co-administered) with the peptide carrier conjugate (such as simultaneously or within about 1-2 hours before or after administration of the peptide carrier conjugate). In a further embodiment, the T-cell epitope peptide is a $CD4^+$ T cell epitope peptide.

An immunogenic composition comprises a plurality of peptide carrier conjugates. A plurality of peptide carrier conjugates may comprise of peptide monomer conjugates, peptide dimer conjugates, trimeric coiled coil conjugates, or any combination thereof. The valency of the immunogenic composition can be varied by the representation of peptide carrier conjugates in the composition. By way of example, an immunogenic composition may comprise trimeric coiled-coil peptides that are only conjugated to a first hapten. In another example, an immunogenic composition may comprise a mixture of trimeric coiled-coil peptides that are conjugated to a first hapten and an analog of the first hapten. An individual trimeric coiled-coil peptide may be conjugated to only the first hapten or the analog, or an individual trimeric coiled-coil peptide may be conjugated to both the first hapten and the analog. In yet another example, an immunogenic composition may comprise a mixture of trimeric coiled-coil peptides that are conjugated to a first hapten and a second hapten. An individual trimeric coiled-coil peptide may be conjugated to only the first hapten or the second hapten, or an individual trimeric coiled-coil peptide may be conjugated to both the first hapten and the second hapten.

Subjects may generally be monitored for therapeutic effectiveness using assays suitable for the condition being treated or prevented, which assays will be familiar to those having ordinary skill in the art and are described herein. The level of an immunogen that is administered to a subject may be monitored by determining the level of the immunogen, in a biological fluid, for example, in the blood, blood fraction (e.g., serum), and/or in the urine, and/or other biological sample from the subject. Any method practiced in the art to detect the immunogen may be used to measure the level of immunogen during the course of an immunization regimen.

The dose of an immunogen described herein for evoking a specific immune response may depend upon the subject's condition, that is, stage of the addiction or disease if present, severity of symptoms caused by the addiction or disease, general health status, as well as age, gender, and weight, and other factors apparent to a person skilled in the medical art. Immunogenic compositions may be administered in a manner appropriate to the addiction, disease or disorder to be treated or prevented as determined by persons skilled in the medical arts. An appropriate dose and a suitable duration and frequency of administration will be determined by such factors as the condition of the patient, the type and severity of the patient's addiction or disease, the particular form of the active ingredient, and the method of administration. Optimal doses of an immunogen may generally be determined using experimental models and/or clinical trials. The optimal dose may depend upon the body mass, weight, or blood volume of the subject. The use of the minimum dose that is sufficient to provide an effective immune response is usually preferred. Design and execution of pre-clinical and clinical studies for an agent (including when administered for prophylactic benefit) described herein are well within the skill of a person skilled in the relevant art. For example, an amount of an immunogen may be administered at a dose between 0.01 mg/kg and 1000 mg/kg (e.g., about 0.1 to 1 mg/kg, about 1 to 10 mg/kg, about 10-50 mg/kg, about 50-100 mg/kg, about 100-500 mg/kg, or about 500-1000 mg/kg) body weight. In another example, an immunogen may be administered at a dose of between 1 and 500 µg. In certain embodiments, an immunogen may be administered at a dose of about 1 µg-10 µg, 10 µg-50 µg, 50 µg-100 µg, or 100 µg-500 µg.

The immunogenic compositions may be administered to a subject in need thereof by any one of several routes that effectively deliver an effective amount of the immunogen. Such administrative routes include, for example, oral, topical, parenteral, enteral, rectal, intranasal, buccal, sublingual, intramuscular, transdermal, vaginal, rectal, or by intracranial injection, or any combination thereof. Such compositions may be in the form of a solid, liquid, or gas (aerosol). The administrative route is also determined by the type of immunogen being administered. In certain embodiments, the immunogenic composition is administered intramuscularly.

Pharmaceutical acceptable excipients (i.e., non-toxic materials that do not interfere with the activity of the active ingredient) are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the immunogenic composition. In addition, antioxidants and suspending agents may also be used. In general, the type of excipient is selected based on the mode of administration, as well as the chemical composition of the active ingredient(s). Alternatively, compositions described herein may be formulated as a lyophilizate, or the immunogen may be encapsulated within liposomes using technology known in the art. Immunogenic compositions may be formulated for any appropriate manner of administration described herein and in the art.

A composition (e.g., for oral administration or delivery by injection) may be in the form of a liquid. A liquid immunogenic composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

For oral formulations, an immunogen described herein can be used alone or in combination with appropriate additives to make tablets, powders, granules or capsules, and if desired, with diluents, buffering agents, moistening agents, preservatives, coloring agents, and flavoring agents. An immunogen included in the compositions may be formulated for oral delivery with a buffering agent, flavoring agent, e.g., in a liquid, solid or semi-solid formulation and/or with an enteric coating.

A composition comprising any one of the immunogens described herein may be formulated for sustained or slow release. Such compositions may generally be prepared using well known technology and administered by, for example, oral, rectal or subcutaneous implantation, or by implantation at the desired target site. Sustained-release formulations may contain the immunogen dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active agent contained within a sustained release formulation depends upon the site of implantation, the rate and expected duration of release, and the nature of the condition to be treated or prevented.

Kits with unit doses of an immunogen described herein, usually in oral or injectable doses, are provided. Such kits may include a container containing the unit dose, an informational package insert describing the use and attendant benefits of the immunogen or antibody in treating pathological condition of interest, and optionally an appliance or device for delivery of the composition.

Adjuvants

The immunogenic compositions described herein may also comprise a pharmaceutically acceptable adjuvant. An adjuvant is intended to enhance (or improve, augment) the immune response to the immunogens described herein, the peptide monomer conjugates, peptide dimer conjugates, or trimeric coiled-coil peptide conjugates (i.e., increase the level of the specific immune response in a statistically, biologically, or clinically significant manner compared with the level of the specific immune response in the absence of administering the adjuvant).

Vaccine adjuvants control the magnitude and quality of adaptive T and B cell responses by facilitating antigen/plasmid uptake into antigen presenting cells and stimulating innate pathways that control leukocyte recruitment to the site of injection (see, e.g., Carter and Reed, 2010, *Curr. Opin. HIV AIDS* 5:409-13). Until 2009, the only licensed adjuvant in the United States, and the only adjuvant used in nicotine vaccine clinical studies, has been aluminum-based mineral salts. More recent evidence suggests that adjuvant formulations that bind innate pattern recognition receptors on APC may provide an equivalent immune response as alum or a greater immune response than alum. Molecules that may be useful as adjuvants include a Toll-like receptor agonists. Toll-like receptors (TLRs) bind molecules characteristic of extracellular pathogens, such as LPS (TLR4), lipoproteins (TLR1, TLR2, TLR6), and flagellin (TLR5), as well intracellular pathogens, such as single-stranded RNA (TLR7, TLR8), double stranded RNA (TLR3) and CpG motif DNA (TLR9) (see, e.g., Mifsud et al., 2014, *Front. Immunol.* 5:79).

For administration in humans, a pharmaceutically acceptable adjuvant is one that has been approved or is approvable for human administration by pertinent regulatory bodies. For example, as discussed herein and known in the art, Complete Freund's adjuvant is not suitable for human administration. Desired adjuvants augment the response to the immunogen without causing conformational changes in the immunogen that might adversely affect the qualitative immune response. Suitable adjuvants include aluminum salts, such as alum (potassium aluminum sulfate), or other aluminum containing adjuvants such as aluminum hydroxide, aluminum phosphate, or aluminum sulfate. Other pharmaceutically suitable adjuvants include nontoxic lipid A-related adjuvants such as, by way of non-limiting example, nontoxic monophosphoryl lipid A (see, e.g., Persing et al., *Trends Microbiol.* 10:s32-s37 (2002)), for example, 3 De-O-acylated monophosphoryl lipid A (MPL) (see, e.g., United Kingdom Patent Application No. GB 2220211). Other useful adjuvants include QS21 and QuilA that comprise a triterpene glycoside or saponin isolated from the bark of the *Quillaja saponaria* Molina tree found in South America (see, e.g., Kensil et al., in *Vaccine Design: The Subunit and Adjuvant Approach* (eds. Powell and Newman, Plenum Press, N Y, 1995); U.S. Pat. No. 5,057,540). Other suitable adjuvants include oil in water emulsions, optionally in combination with immune stimulants, such as monophosphoryl lipid A (see, e.g., Stoute et al., *N. Engl. J. Med.* 336, 86-91 (1997)). Other suitable adjuvants include polymeric or monomeric amino acids such as polyglutamic acid or polylysine, liposomes, and CpG (see, e.g., Klinman, *Int. Rev. Immunol.* 25(3-4):135-54 (2006); U.S. Pat. No. 7,402,572; European Patent No. 772 619). Other suitable adjuvants include toll-like receptor agonists that bind to TLR4, TLR1, TLR2, TLR6, TLR5, TLR7, TLR8, TLR3, and TLR9 (see, e.g., Mifsud et al., 2014, *Front. Immunol.* 5:79; Steinhagen et al., 2011, *Vaccine* 29:3341-3355). Such TLR based adjuvants include, for example, glucopyranosyl lipid A-stable emulsion (GLA-SE) (U.S. Pat. No. 8,609,114; Coler et al., 2010, *PLoS One* 4:e13677); AS04 (see, e.g., Didierlaurent et al., 2009, *J. Immunol.* 183:6186-6197); imiquimod (see, e.g., Bernstein et al., 1995, *Vaccine* 13:72-6); and CpG7909 (Mullen et al., 2008, *PLoS One* 3:e2940). In certain embodiments, the immunogenic compositions described herein comprise an adjuvant that is a toll-like receptor (TLR) agonist. In a specific embodiment, the adjuvant is a glucopyranosyl Lipid A-Stable Emulsion (GLA-SE) adjuvant. In other embodiments, the adjuvant is an aluminum based adjuvant.

Use and Characterization of Immunogenic Compositions

Also provided herein are methods for inducing an immune response specific for a hapten, comprising administering to the subject any of the immunogenic compositions described herein. A subject includes a rodent, a mouse, a rat, a rabbit, a monkey, a dog, a cat, a sheep, cattle, a non-human primate, a pig, and a human. In certain embodiments, a subject is a human. To evaluate the immunogenicity of any one of the immunogens or immunogenic compositions described herein, the immunogen may be administered to a subject by a parenteral (e.g., intravenous), intraperitoneal, intramuscular, intradermal, intraocular, or subcutaneous route. The immunogenic composition may further comprise a suitable adjuvant to enhance the immune response to the immunogen. See, e.g., Harlow et al., *Antibodies: A Laboratory Manual*, Cold Spring Harbor Laboratory (1988). Adjuvants typically used for immunization of non-human animals include but are not limited to Freund's complete adjuvant, Freund's incomplete adjuvant, montanide ISA, Ribi Adjuvant System (RAS) (GlaxoSmithKline, Hamilton, Mont.), and nitrocellulose-adsorbed antigen. In general, after the first injection, subjects receive one or more booster immunizations according to a preferred schedule that may vary according to, inter alia, the immunogen, the adjuvant (if any) and/or the particular species of subject. The B cell immune response may be monitored by periodically bleeding the subject, separating the sera from the collected blood, and analyzing the sera in an immunoassay, such as an ELISA or Ouchterlony diffusion assay, or the like, to determine the specific antibody titer. When an adequate antibody titer is established, the subject may be bled periodically to accumulate the polyclonal antisera.

In general, to monitor the immune response of an immunized host during pre-clinical studies in subjects, sera is obtained from the subjects prior to the first dose (i.e., pre-immune sera) and obtained after the final boosting dose. Sera may also be obtained after any one or more of the boosting doses between the primary dose and final boosting dose. To monitor the immune response of an immunized host during clinical studies or during post-marketing studies, sera may also be obtained from humans before the first immunization and after one or more administrations of the immunogenic compositions.

Production of antigen-specific antibodies in an immunized host (including a human host) may include production of any class of immunoglobulin, including IgG, IgA, IgM, and/or IgE, and isotypes within the classes. The presence of specific IgG, IgM, IgE, and IgA may be detected in a biological sample (e.g., serum, nasal wash, lung lavage, or other tissues) obtained from an immunized host. For detection of antibodies in an immunoassay, the biological sample may be permitted to interact with or contact an antigen that is purified, isolated, partially isolated, or a fragment thereof.

Production of antigen specific T cells in an immunized host (including a human host) may include production of any type of T cells, including CD4+ T cells and CD8+ T cells. The presence of specific CD4+ or CD8+ T cells may be detected in a biological sample obtained from an immunized host. Assays for measurement of T cell responses are known to those skilled in the art and include, for example, T cell proliferation assays, cytokine based assays (e.g., ELISA, cytokine ELISPOT, intracellular cytokine staining), flow cytometry, cytometry by time of flight (CyTOF) mass spectroscopy, MHC tetramer staining, and cytotoxicity assays (see, e.g., Saade et al., 2012, $Expert\ Rev.\ Vaccines$ 11:1459-70; Nagorsen et al., 2004, $Expert\ Opin.\ Biol.\ Ther.$ 2004, 4:1677-84; DeRosa, 2012, $Methods$ 57:383-91). The immunogenicity of immunogens described herein may also be characterized by any number of assays and techniques practiced in the art, including immunoassays to evaluate binding and the capability of the immunogen to induce an immune response. By way of non-limiting example, immunoassays include ELISA, immunoblot, radioimmunoassay, immunohistochemistry, fluorescence activated cell sorting (FACS), Ouchterlony, proliferation assays, cytotoxicity assays, MHC peptide tetramer staining, intracellular cytokine staining, cytokine ELIspot, and the like. Conditions for in vitro assays include temperature, buffers (including salts, cations, media), and other components that maintain the integrity of any cell used in the assay and the compound, which a person skilled in the art will be familiar and/or which can be readily determined. A person skilled in the art also readily appreciates that appropriate controls can be designed and included when performing the in vitro methods and in vivo methods described herein.

In vitro assay methods typically comprise contacting the biological sample with at least one source of the antigens described above and herein under conditions and for a time sufficient for an antibody in the sample to interact with the antigen source (i.e., mixing, combining, or in some manner permitting the biological sample and the antigen to interact). An antibody present in the biological sample that specifically binds to the antigen can be detected using any one of the exemplary detection methods described herein and in the art for detecting antibody-antigen binding. By way of non-limiting example, antibody bound to the antigen may be detected using a reagent specific for a conserved region of the antibody, such as the Fc portion of the antibody, which reagent is typically selected depending on the source of the antibody (i.e., whether the antibody is from an animal, such as a mouse, rat, goat, or sheep, etc. or whether the antibody is from a human). Such reagents typically comprise a detectable label, for example an enzyme, fluorescent label, luminescent label, or radioactive label. Additional exemplary reagents include those that detect a specific isotype or class of antibody. Many such reagents may be obtained from commercial sources.

EXAMPLES

Example 1

Preparation of Trimeric Coiled Coil Conjugates

A 37 and 65 amino acid amphipathic α-helical peptide (SEQ ID NOS: 1 and 2) were synthesized (Biosynthesis, Inc., Lewisville, Tex.) with 16 or 26 surface-exposed lysines, respectively. An amphipathic α-helical peptide (SEQ ID NO: 1) was linked in tandem to a pan HLA DR binding epitope (PADRE) (SEQ ID NO:10) (see, e.g., La Rosa et al., 2012, $J.\ Infect.\ Dis.$ 205:1294-304) that in turn was linked to an influenza virus subtype A H5N1 hemagglutinin peptide MHC Class II epitope (SEQ ID NO:6) (see, e.g., Clegg et al. 2012, $Proc.\ Natl.\ Acad.\ Sci.\ USA$ 109: 17585-90). The amino acid sequence of this amphipathic α-helical peptide/PADRE epitope/CD4+ T cell hemagglutinin peptide epitope has 62 amino acids and is set forth in SEQ ID NO:13.

The amphipathic α-helical peptides of SEQ ID NO:1 and SEQ ID NO:2 were also each tandemly linked to an OVA-derived $H2D^d$ restricted T cell epitope (SEQ ID NO:7; see, e.g., Sant et al., 2013, $Front.\ Immunol.$ 4:340). The amino acid sequence of the amphipathic α-helical peptide (SEQ ID NO: 1; 37 amino acids)/CD4+ T cell OVA peptide epitope peptide carrier (TCC16) is set forth in SEQ ID NO:14. The amino acid sequence of the amphipathic α-helical peptide (SEQ ID NO:2; 65 amino acids)/CD4+ T cell OVA peptide epitope peptide carrier (TCC26) is set forth in SEQ ID NO:15.

Trimeric coiled coil (TCC) structures comprising (1) three peptide monomers having an amino acid sequence set forth in SEQ ID NO:13; (2) three peptide monomers having an amino acid sequence set forth in SEQ ID NO: 14; and (3) three peptide monomers having an amino acid sequence set forth in SEQ ID NO:15 were prepared by allowing the trimeric structures to self-assemble spontaneously following the addition of water or buffer such as PBS to the lyophilized peptides. After self-assembly into trimeric coiled coil structures, peptide lysine residues in the TCC were conjugated to nicotine 6-hexanoic acid (N-6-HA). To conjugate nicotine to trimeric coiled coil peptides, a linker moiety is added to the nicotine molecule. For the experiments described herein synthesis of the nicotine-linker molecule N-6-HA was performed as illustrated in the schematic shown in FIG. 1A. Conjugation of N-6-HA to the trimeric coiled coil peptides was performed by using ethyl (dimethylaminopropyl) carbodiimide (EDC)/N-hydroxysuccinimide (NHS) chemistry. The trimeric coiled coil molecules were loaded with an average of 0.6, 4, 6, 7, 14, or 26 nicotines (abbreviated as Nic0.6, Nic4, Nic6, Nic7, Nic14, Nic26, respectively) per peptide. Trimeric coiled coil structures comprising three peptide monomers having an amino acid sequence set forth in SEQ ID NO:13 were also conjugated with nicotine to provide constructs comprising an average of 0.6, 4, and 14 nicotine molecules per monomeric peptide. These constructs are called $TCC^{Nic0.6}$, $TCC^{Nic4}$, and $TCC^{Nic14}$ herein.

UV spectroscopy based hapten quantification was used to measure nicotine conjugation. UV absorbance of the TCC- Nic peptides were measured from 220-320 nm. Nicotine conjugation to each carrier was quantified as previously described (Hamblett et al. 2004, *Clin. Cancer Res.* 10:7063-7070, see also, Miller et al., 2014, *PLOS ONE*, 9:e114366, incorporated herein by reference, in their entirety), using extinction coefficients at A280 nm calculated by the ProtParam software program (Gasteiger et al., 2003, *Nucleic Acids Res.* 31:3784-3788) for the hapten carriers (e.g. 25,440 $M^{-1}$ $cm^{-1}$ at 280 nm and 20,274 $M^{-1}$ $cm^{-1}$ at 264 nm for the TCC peptide), and a molar extinction coefficient of 2,959 $M^{-1}$ $cm^{-1}$ for nicotine-6-HA at 264 nm and 270 $M^{-1}$ $cm^{-1}$ at 280 nm. Thus, to calculate the average nicotine:TCC peptide molar ratios, the absorbance of TCCnic was measured at 264 and 280 nm and the values inserted into the equation described by Hamblett et al. In certain instances, the conjugated TCC peptide carriers were combined with the adjuvant, Toll-like receptor 4 agonist glucopyranosyl lipid adjuvant-stable emulsion (GLA-SE), or Alum adjuvant. A control conjugated vaccine used in experiments described herein employed keyhole limpet hemocyanin (KLH) as a carrier (see, e.g., Pryde et al., 2013, PLoS One 8:e76557) and had an average of 22 nicotines per monomer ($KLH^{Nic22}$), which is a load level similar to most preclinical and clinical vaccines presently studied (see, e.g., Pentel and LeSage, 2014, *Adv. Pharmacol.* 69:553-80).

Example 2

Trimeric Coiled-Coil-Nicotine Constructs Induce High Nicotine-Specific Antibody Titers Trimeric coiled coil structures comprising three peptide monomers having an amino acid sequence set forth in SEQ ID NO:13 were conjugated as described above with nicotine to provide constructs comprising an average of 0.6, 4, and 14 nicotine molecules per monomeric peptide. These constructs are called $TCC^{Nic0.6}$, $TCC^{Nic4}$, and $TCC^{Nic14}$ herein. C57BL/6 mice (n=5/group) were immunized with the TCC constructs or $KLH^{Nic22}$ either alone or with an adjuvant, either Alum or GLA-SE. Mice were immunized at days 0, 14, and 146 with 2.5 µg of the trimeric coiled-coil peptide conjugates. Control groups were administered KLH-Nic22 or PBS. Sera were collected periodically for approximately 20 weeks after the primary immunization, and anti-nicotine antibody titers were determined by ELISA. Representative data, which were generated from the sera of mice immunized with $TCC^{Nic4}$, are presented in FIG. 3. Both adjuvanted conjugated carriers induced robust antibody titers that remained near maximal titers throughout the experiment. The titer in animals immunized with $TCC^{Nic4}$ was consistently greater than in animals immunized with $KLH^{Nic22}$ (see FIG. 3).

Figure 4:
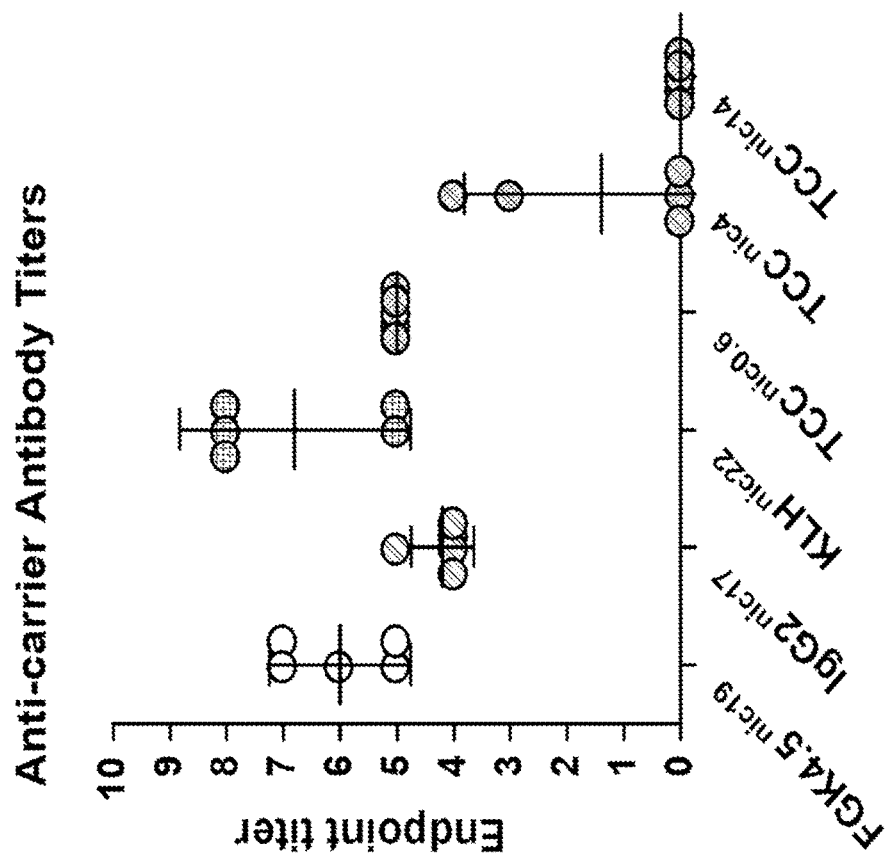
FIG. 4 presents level of antibodies specific for the carrier moiety in animals immunized with nicotine conjugated to carrier. C57Bl/6 mice (n=5/group) received primary and booster immunizations with three control nicotine vaccines (FGK4.5$^{nic19}$, IgG2$^{nic17}$, and KLH$^{nic22}$) adjuvanted with GLA-SE and three TCC vaccines containing on average 0.6, 4, and 14 nicotines per peptide monomer adjuvanted with GLA-SE. Sera isolated on day 35 were assayed for antibodies that specifically bound to each hapten carrier.

In the same experiment, groups of mice were immunized with three non-TCC nicotine carriers, $FGK4.5^{nic19}$ and $IgG2^{nic17}$ and $KLH^{nic22}$. Groups of animals were also immunized with $TCC^{Nic0.6}$, $TCC^{Nic4}$, and $TCC^{Nic14}$. Sera were obtained from immunized animals and tested for the presence of antibodies to the various nicotine carriers. Sera were collected and measured for anti-nicotine and anti-carrier antibody titers by ELISA using, respectively, nicotine conjugated BSA, non-conjugated trimeric coiled-coil peptide, and non-conjugated KLH, FGK4.5, and IgG2 carriers used in the respective vaccine composition. Each sample was assayed in triplicate wells along with standard control sera, and the mean midpoint and endpoint titers (+/–SEM) were determined. The results are presented in FIG. 4. Trimeric coiled-coil peptide conjugates with higher nicotine loads induced lower anti-carrier (i.e., anti-TCC) antibody titers (see FIG. 4). The results of this study suggest that the trimeric coiled-coil peptide conjugate is less likely to result in suppression of the immune response to nicotine relative to currently used nicotine carriers.

Figure 5:
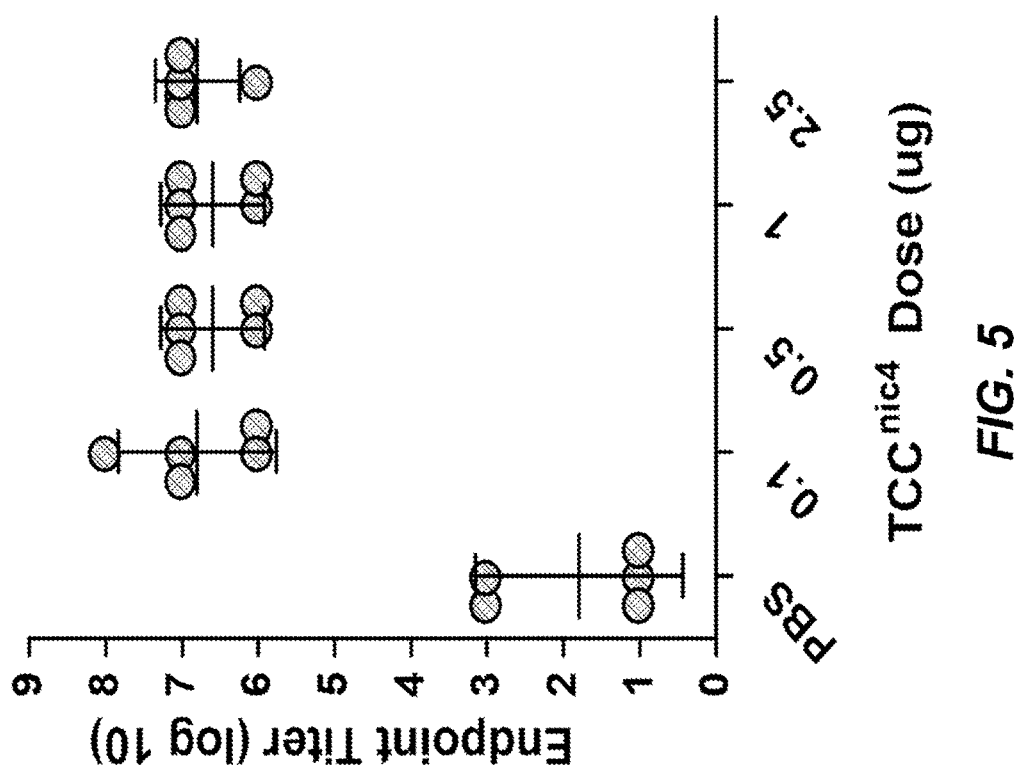
FIG. 5 illustrates titer to nicotine in mice (C57Bl/6 mice (n=5/group)) immunized with the indicated doses of TCC$^{Nic4}$ plus GLA-SE adjuvant. Day 35 sera were assayed for anti-nicotine antibodies by ELISA.

The maximum anti-nicotine antibody response was achieved with as little as 100 ng of a TCC conjugate adjuvanted with GLA-SE as shown in FIG. 5. Mice were immunized with 0.1, 0.5, 1, or 2.5 µg $TCC^{nic4}$. This result in combination with the observation from FIG. 3 that booster immunizations do not substantially increase antibody titers over time implies that the vaccine has activated the full complement of lymphocytes capable of recognizing the nicotine hapten.

The immunogenicity of two additional trimeric coiled-coil peptide conjugates was also tested in BALB/c mice. One trimeric coiled-coil was comprised of 3 peptide monomers that were each 50 amino acids in length with 16 lysine residues (TCC16). A second trimeric coiled-coil peptide was 78 amino acids in length with 26 lysine residues (TCC26). Each comprised an OVA-derived $H2D^d$ restricted CD4+ T cell epitope (see, e.g., Sant et al., 2013, *Front. Immunol.* 4:340) at the C-terminus (SEQ ID NOS: 14 and 15, respectively described above in Example 1). Each trimeric coiled-coil peptide carrier was loaded with variable numbers of nicotine molecules (e.g., 6, 7, 14, or 24 to provide ($TCC16^{Nic6}$, $TCC16^{Nic14}$, $TCC26^{Nic7}$, and $TCC26^{Nic24}$, respectively). BALB/c mice (n=5/group) received a primary intramuscular immunization with 2.5 µg of $TCC16^{Nic6}$, $TCC16^{Nic14}$, $TCC26^{Nic7}$, $TCC26^{Nic24}$, or PBS as a negative control, followed by booster immunizations with the same vaccines on day 14. Mice were also immunized with KLH-Nic22 for comparison.

Figure 12:
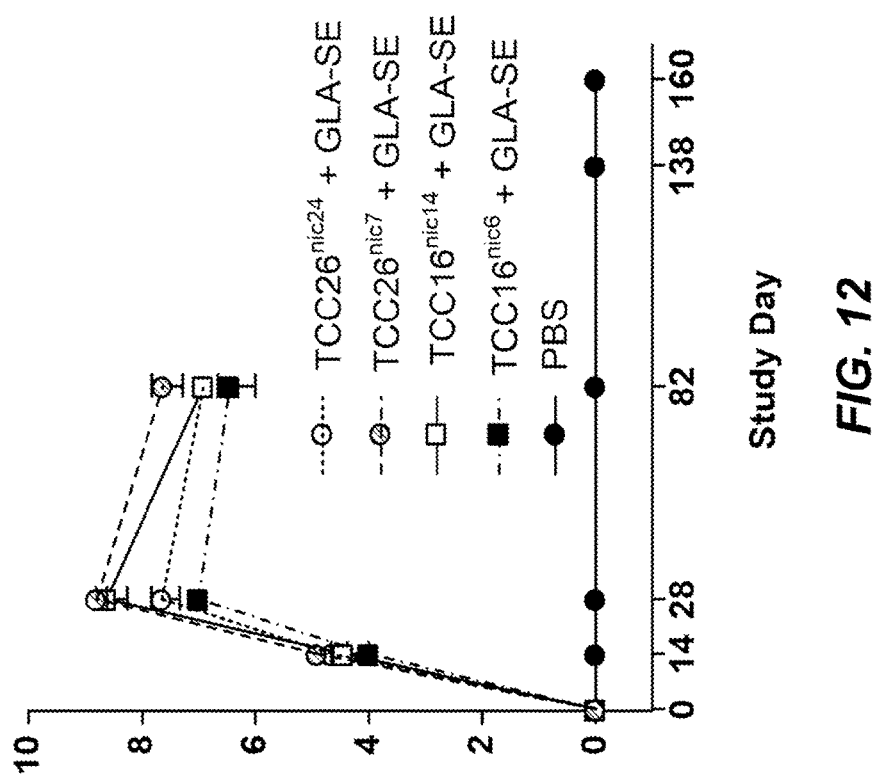
FIG. 12 shows titer of antisera from animals (BALB/c mice (n=5/group)) immunized on day 0 and day 14 with 2.5 μg of the indicated TCC carriers. Anti-nicotine antibody titers were analyzed by ELISA. TCC16 represents a trimeric coiled-coil peptide vaccine comprising three peptide monomers of 50 amino acids in length with 16 lysines per peptide monomer. TCC16 was conjugated with an average of 6 or 14 haptens per peptide monomer (TCC16$^{Nic6}$, TCC16$^{Nic14}$, respectively). TCC26 represents a trimeric coiled-coil peptide vaccine comprising three peptide monomers of 78 amino acids in length with 26 lysines per peptide monomer. TCC26 was conjugated with an average of 7 or 24 haptens per peptide monomer (TCC26$^{Nic7}$, TCC26$^{Nic24}$, respectively). Each TCC peptide monomer also contained an H2D$^d$ restricted T cell epitope for activity in BALB/c mice.

As shown in FIG. 12, each trimeric coiled-coil peptide conjugate induced similar high antibody titers in the presence of GLA-SE, regardless of nicotine loading level. These results demonstrate the versatility of the trimeric coiled-coil peptide conjugate platform and show that the trimeric coiled-coil peptide conjugate can induce similar responses regardless of peptide length and hapten loading level.

Example 3

Antibody Affinity and Nicotine Binding Capacity

Antibody affinity and the nicotine binding capacity of the anti-nicotine antibodies evoked in $TCC^{Nic4}$-immunized mice were examined. Mice were immunized with 2.5 µg $TCC^{Nic4}$ on days 0, 14, and 146, and antisera were obtained. Nicotine binding to antisera isolated from $TCC^{Nic4}$ immunized mice was determined by competitive ELISA for nicotine, cotinine, and acetylcholine.

Figure 6:
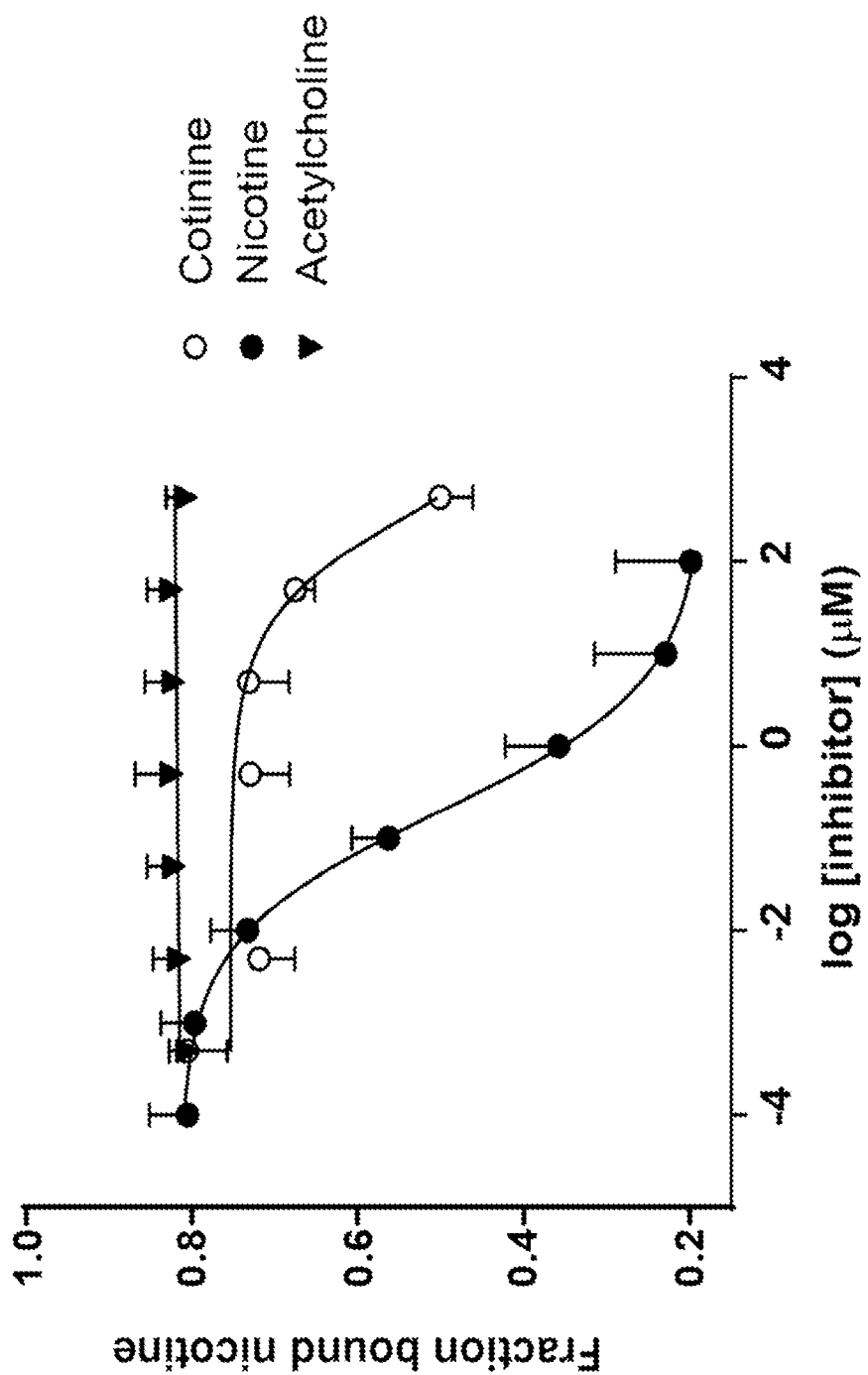
FIG. 6 presents data showing specificity of nicotine binding by antisera isolated from TCC$^{Nic4}$ immunized mice determined by competitive ELISA for nicotine, cotinine, and acetylcholine.

The antibodies induced by immunization ($TCC^{Nic4}$) were nicotine-specific and did not bind physiological concentrations of cotinine, the most abundant metabolite in the nicotine degradation pathway. The antibodies also did not bind to acetylcholine, which is the endogenous nicotine receptor ligand. These data are presented in FIG. 6. $IC_{50}$ values for cotinine were 1000-fold greater than nicotine. $IC_{50}$ values could not be calculated for acetylcholine due to a lack of inhibition.

Figures 7A, 7B:
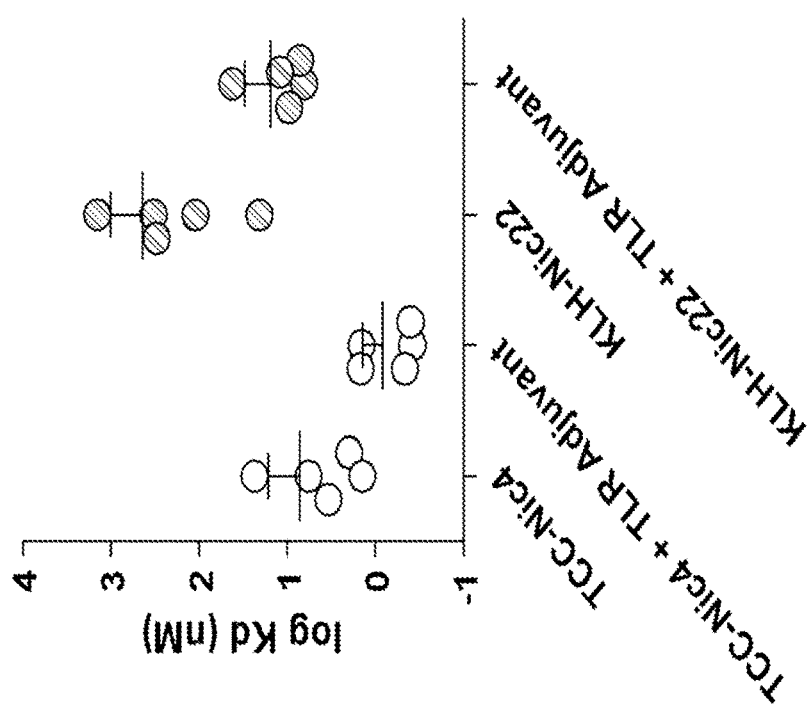
FIGS. 7A-B illustrate antibody avidities of antisera from mice immunized with TCC conjugated to nicotine. $K_d$ values of anti-nicotine antibodies were determined by competitive ELISA and are shown in FIG. 7A. The mean $K_d$ values are presented in FIG. 7B.

Relative $K_d$ values of serum IgG were determined by competitive ELISA. Dilutions of antiserum were prepared and incubated with soluble nicotine (0.0001-100 µM). After equilibrium was achieved, binding to bovine serum albumin (BSA) conjugated to nicotine was measured. This procedure is a modification of published procedures (see, e.g., Friguet et al., 1985, *J. Immunol. Methods* 77:305-19; Seligman, 1994, *J. Immunol. Methods* 168:101-10; Stevens, 1987, *Mol. Immunol.* 24:1055-60) that allows determining antibody affinities in the low nM range, which are comparable to affinities obtained using RIA procedures. Each sample was assayed in triplicate wells along with standard control sera, and the mean midpoint and endpoint titers (+/−SEM) were determined. Antibody affinity measurements (see FIG. 7A-B) showed that in the absence of adjuvant, $TCC^{Nic4}$ induced higher affinity antibodies compared to $KLH^{Nic22}$. In the presence of GLA-SE adjuvant, the affinity of the antibodies evoked by immunization with $TCC^{Nic4}$ increased even further to about 1 nM and was an order of magnitude greater than antibodies evoked by $KLH^{Nic22}$.

Example 4

In Vivo Analysis of Trimer Coiled-Coil-Nicotine Construct

To test antibody function, $TCC^{Nic4}$ or $KLH^{Nic22}$ (non-adjuvanted; +Alum; or +GLA-SE) immunized mice were injected with free nicotine equivalent to 3 cigarettes. On day 196 after mice were immunized, the mice were injected with 0.05 mg/kg of nicotine hydrogen tartrate. This nicotine dose is equivalent to approximately three smoked cigarettes (see, e.g., Matta et al., 2007, *Psychopharmacology* 190:269-319). Blood was collected five minutes after nicotine infusion in anesthetized animals, and plasma was prepared. Following exsanguination, animals were perfused with PBS and the brain was harvested, weighed, sectioned, and then frozen. Nicotine was extracted from the plasma and brain tissues and then quantified by LC/MS. The amounts of nicotine in plasma (ng/ml) and brain (ng/g) were determined. The proportion of nicotine sequestered specifically in the blood provides a measure of immunogen efficacy. Data were analyzed using GraphPad Prism (San Diego, Calif.). Statistically significant differences between 2 groups were calculated by Student's 2-tailed t-test on log transformed data and between 3 or more groups by 1-factor analysis of variance (ANOVA) followed by post-hoc analysis. Differences were considered significant with p<0.05.

Plasma was assayed for nicotine binding capacity at various times following immunization. Plasma aliquots were spiked with increasing nicotine levels (0.0001-10 μM) (serum nicotine levels in heavy smokers is 100 ng/ml or 0.617 μM) and then subjected to inhibition RIA (with $H^3$-Nicotine as the tracer and non-radiolabeled nicotine as the inhibitor) to calculate the total nicotine binding IgG in serum (see, e.g., Moreno et al., 2010, *Mol. Pharm.* 7:431-41; Muller, 1983, *J Methods Enzymol.* 92:589-601). Immobilized protein A was used to capture IgGs from the serum to separate them from free nicotine. Aliquots of both the protein A eluate and the serum supernatant were subjected to liquid scintillation counting to quantify the amount of tracer in each fraction.

Figure 8:
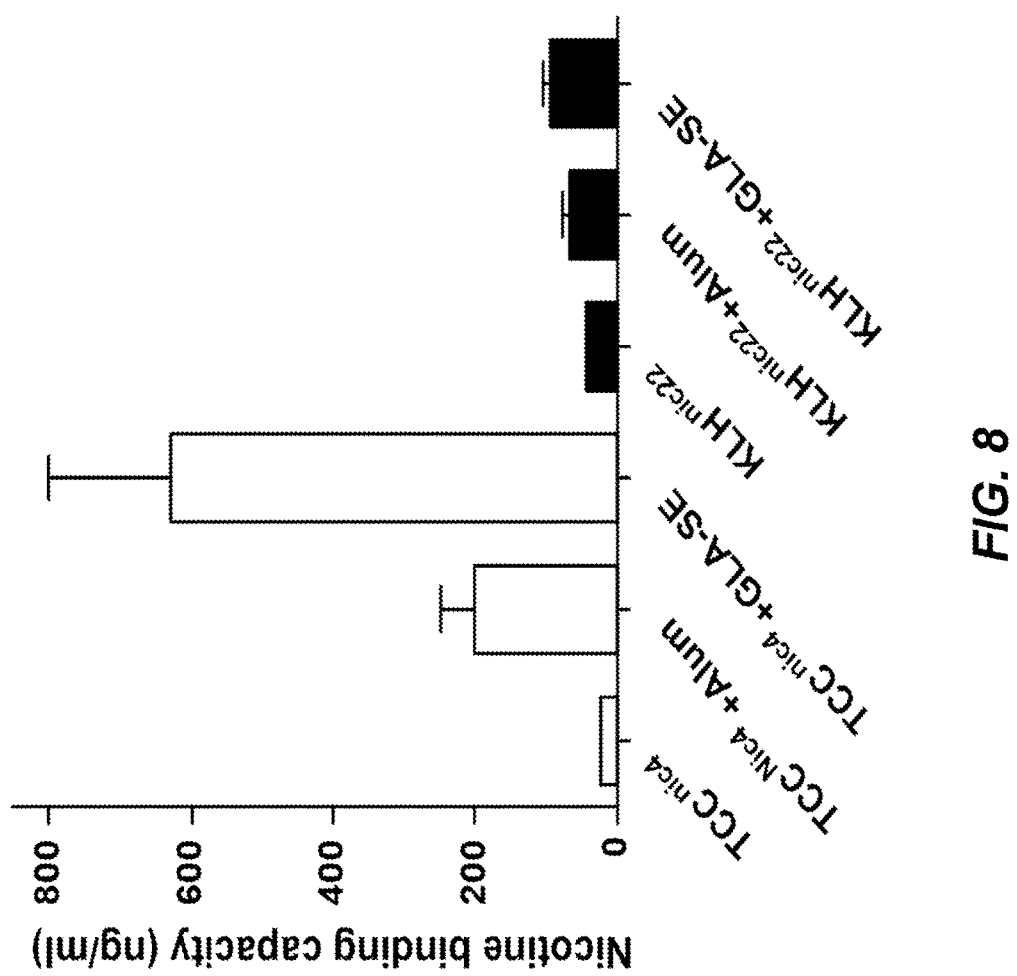
FIG. 8 shows serum nicotine binding capacity of immunized mice determined by measuring bound and free concentrations of nicotine at equilibrium. $K_d$ values were used to calculate total antibody concentrations according to the law of mass action equation: $K_d=[\text{Nic}][\text{Ig}]/[\text{Nic-Ig}]$.

The higher antibody titers and affinities observed in $TCC^{Nic4}$ immunized mice contributed to a significantly larger nicotine binding capacity than observed in the control $KLH^{Nic2}$ immunized mice as shown in FIG. 8. Without wishing to be bound by theory, the greater serum binding capacity of antibodies specific for nicotine that are induced by TCC-nicotine conjugates could conceivably bind 10-times the amount of nicotine found in the blood of a heavy smoker (100 ng/ml serum; see, e.g., Raupach et al., 2012, *Drugs* 72:e1-16).

Figures 9A, 9B, 9C:
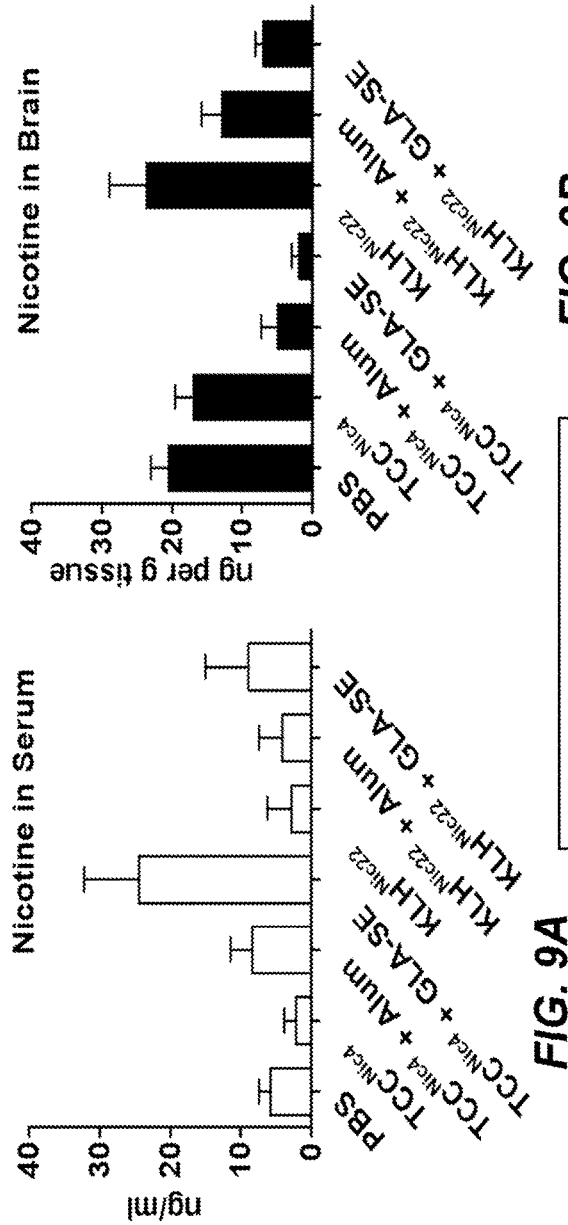
FIGS. 9A-C show the levels of nicotine in sera and brains of mice (n=5/group) immunized with PBS, TCC$^{Nic4}$ with and without alum and GLA-SE adjuvants, or KLH conjugated to nicotine (KLH$^{Nic22}$) with and without alum and GLA-SE adjuvants. Immunized mice were injected with a dose of nicotine tartrate equivalent to the nicotine in 3 cigarettes (1.2 μg). Five minutes later the mice were sacrificed, tissues removed, and the amount of nicotine in (A) sera and (B) brain were measured by mass spectrometry. (C) The calculated percent inhibition of nicotine entry into the brain is shown.
Figure 10A:
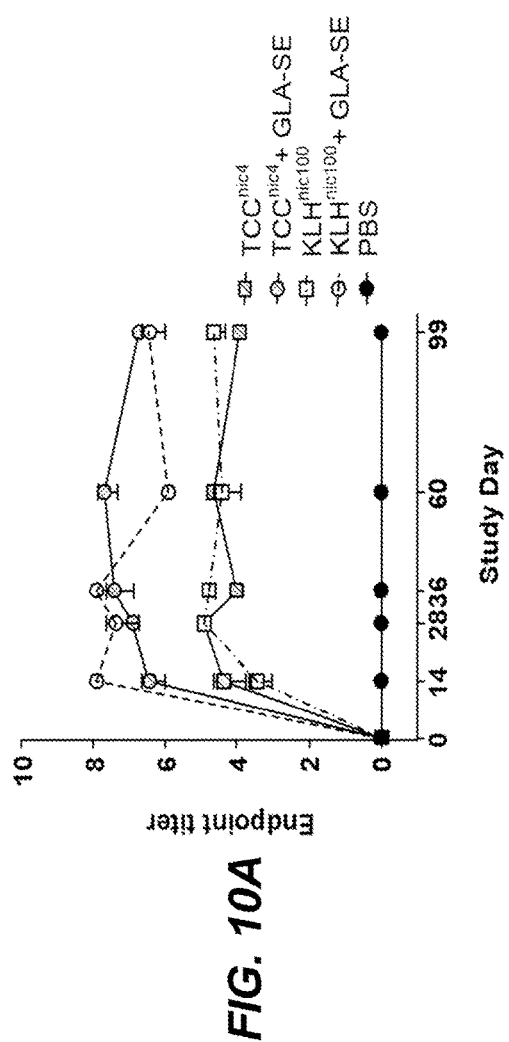
FIGS. 10A-B show comparative antibody responses between TCC$^{Nic4}$ and KLH$^{Nic100}$. C57Bl/6 mice were immunized with each conjugate in the absence and presence of GLA-SE adjuvant. (A) Serum was assayed for anti-nicotine antibody responses by ELISA. (B) Data showing serum sequestration of nicotine. Percent inhibition of nicotine entry into the brain is indicated.
Figure 10B:
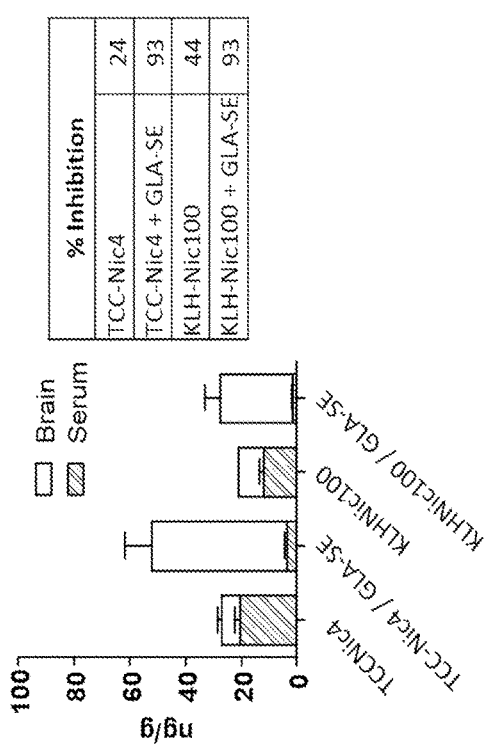

Consistent with data illustrating antibody binding capacity of antibodies evoked by TCC conjugates, $TCC^{Nic4}$ was a superior immunogen compared with $KLH^{Nic22}$ when combined with either adjuvant (see FIGS. 9A-B). Moreover, $TCC^{Nic4}$ plus GLA-SE adjuvant induced an antibody response that could prevent greater than 90% of circulating nicotine from entering the brain (see FIG. 9C). To confirm that the improved antibody responses resulting from $TCC^{Nic4}$ immunization correlated with hapten loading, $TCC^{Nic4}$ activity was compared with a KLH vaccine containing 5 times the amount of nicotine as $KLH^{Nic22}$ ($KLH^{Nic100}$). As shown in FIG. 10, GLA-SE adjuvanted $KLH^{Nic100}$ induced similar antibody titers as $TCC^{Nic4}$ and comparable levels of functional antibodies as determined by nicotine sequestration in serum.

Figure 11:
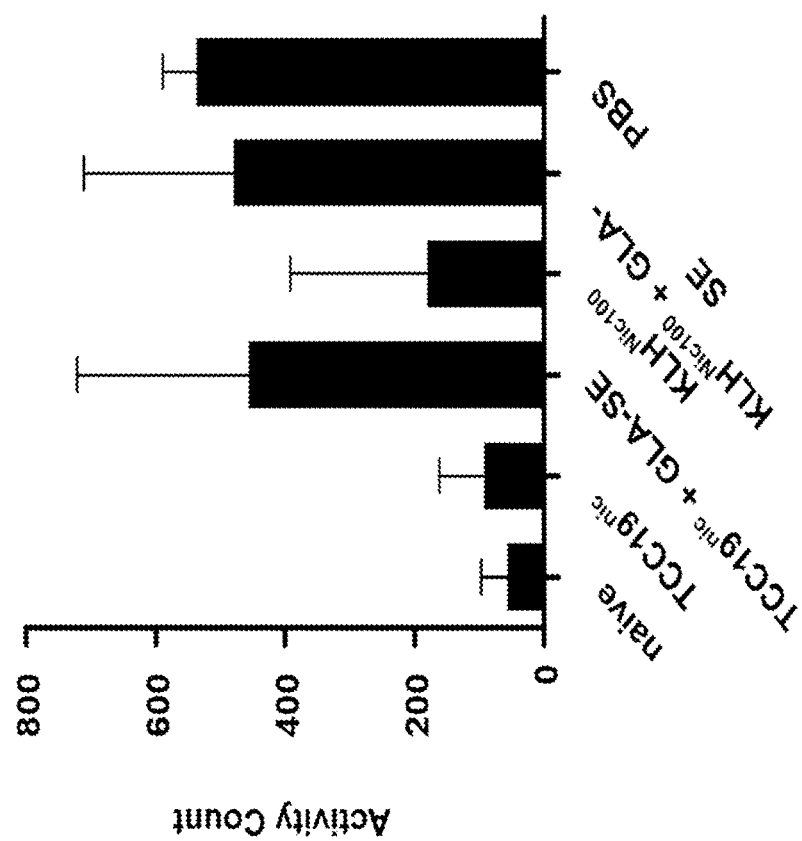
FIG. 11 shows vaccine prevention of nicotine-induced hypoactivity in mice. C57Bl/6 mice were immunized with TCC$^{Nic4}$ and KLH$^{Nic100}$ in the absence and presence of GLA-SE adjuvant. Immunized mice were sensitized to nicotine with 10 daily injections (10 μg). Following a 7 day rest period, mice were challenged with nicotine (10 μg), and locomotor activity was monitored using infrared beam-equipped open field chambers. The PBS-immunized group was not challenged with nicotine.

Furthermore, mice immunized with $TCC^{Nic4}$ and $KLH^{Nic100}$ with and without GLA-SE as described above were evaluated for nicotine-induced hypoactive behavior with nicotine challenges as described in Rosenberg et al. (2013, *Hum. Gene Ther.* 24:595-603). Immunized mice were sensitized with 10 daily injections of 10 μg of nicotine. After a 7 day rest period, the mice were then challenged with 10 μg of nicotine, and locomotor activity was monitored using infrared beam-equipped open field chambers. The mice immunized with PBS were not challenged with nicotine. The adjuvanted vaccines appeared equivalent in preventing nicotine sensitization and subsequent hypoactivity behavior in nicotine challenged mice, in contrast to the hypoactivity observed in sensitized naïve mice and mice immunized with non-adjuvanted vaccine (see FIG. 11).

In summary, these results have shown that a synthetic trimeric coiled coil peptide conjugate of varying lengths and nicotine load can be used to induce functional antibody responses in mice. These trimeric coiled-coil peptide conjugates described herein induced superior antibody responses relative to a more commonly used carrier. In addition, adjuvants enhance the function of trimeric coiled-coil peptide-nicotine conjugates by augmenting both antibody titer and affinity, and GLA-SE was superior to Alum in these experiments.

Example 5

Primate Study: Immunization with Trimer Coiled-Coil-Nicotine Construct

Vaccine Preparation:

A 57 amino acid amphipathic helical peptide is synthesized (Biosynthesis, Inc., Lewisville, Tex.) with 16 surface-exposed lysines. The peptide is linked in tandem to a MHC Class II epitope that was previously shown to activate CD4+ T cell responses in monkeys (see, e.g., Kumar et al., *J Immunol Methods*, 2001. 247(1-2): p. 49-60). After self-assembly, peptide lysines are conjugated to N-6-HA using EDC/NHS chemistry for maximal nicotine loading of approximately 13-16 nicotine molecules per peptide. This vaccine is adjuvanted using the stable oil-in-water emulsion, SE (provided by Infectious Disease Research Institute).

Immunizations:

*C. macaques* monkeys are immunized initially by intramuscular immunization (1 ml) with 5, 10, or 50 μg of TCC-Nic16 adjuvanted with SE (final 2% emulsion), or PBS as a negative control, followed by booster immunizations with the same vaccines on day 22, day 43, and day 92. To monitor safety, animals are observed for overt clinical changes on the day of injection, and the injection site is observed for reactions of redness, swelling and induration. These data are collected 24 hours post immunization and are analyzed using a Draize scores methodology.

ELISA:

Sera are collected every 2 weeks after the first injection and frozen in aliquots for later measurement of anti-nicotine and anti-carrier antibody titers by ELISA. Nicotine conjugated BSA and non-conjugated TCC peptide are used as controls. Each sample is assayed in triplicate wells along with standard control sera, and the mean midpoint and endpoint titers (+/−SEM) are determined. To confirm that anti-TCC antibodies do not prevent induction of subsequent anti-nicotine antibody responses, we will test for correlations between anti-TCC antibody titers prior to the last boost, and the fold increase in anti-nicotine antibody levels following a boost immunization (see, e.g., McCluskie et al., *Int Immunopharmacol.* 2013; 16(1):50-56).

Antibody Affinity:

Relative $K_d$ values of serum IgG are measured by competitive ELISA. Antiserum dilutions are incubated with soluble nicotine (0.0001-100 μM), and following equilibrium, assayed for binding to BSA-Nic by ELISA. The ELISA method is modification of the published procedures (see, e.g., Friguet et al., 1985, *J. Immunol. Methods* 77:305-19; Seligman, 1994, *J. Immunol. Methods* 168:101-10; Stevens, 1987, *Mol. Immunol.* 24:1055-60) allows determination of antibody affinities in the low nM range, which are comparable to affinities obtained using RIA procedures.

Ex Vivo Functional Analysis:

Plasma are assayed for nicotine binding capacity at various times following immunization. Plasma aliquots are spiked with increasing nicotine levels (0.0001-10 μM (serum nicotine levels in heavy smokers is 100 ng/ml or 0.617 μM) and then subjected to inhibition RIA (with $H^3$-Nicotine as the tracer and non-radiolabeled nicotine as the inhibitor) to calculate the total nicotine binding IgG in serum (see procedures in Example 3). Immobilized protein A is used to capture IgGs from the serum to separate them from free nicotine. Aliquots of both the protein A eluate and the serum supernatant are subjected to liquid scintillation counting to quantify the amount of tracer in each fraction.

In Vivo Functional Analysis:

Nicotine distribution in brain and plasma is determined on day 196 following infusion of 0.05 mg/kg of nicotine hydrogen tartrate in anesthetized animals. This nicotine dose is equivalent to approximately three smoked cigarettes (see, e.g., Matta, et al., *Psychopharmacology* (Berl), 2007. 190 (3): p. 269-31). Blood is collected 5 min later and plasma collected. Following exsanguinations, animals are perfused with PBS and the brain harvested, weighed, sectioned, and then frozen. Plasma and tissue samples are prepared, and nicotine is extracted and then quantified by LC/MS. The amounts of nicotine in plasma (ng/ml) and brain (ng/g) are determined, and the proportion of nicotine sequestered specifically in the blood provides a measure of efficacy.

Statistical Analysis:

Data are analyzed using GraphPad Prism (San Diego, Calif.). Statistically significant differences between 2 groups is calculated by Student's 2-tailed t-test on log transformed data and between 3 or more groups by 1-factor analysis of variance (ANOVA) followed by post-hoc analysis. Differences are considered significant with $p<0.05$.

Example 6

Characterization of Different Nicotine Hapten-Linker Combinations

Nicotine Haptens and Linkers:

Nicotine haptens having an amino group added to the 6- or 5-position of the nicotine pyridine ring (H1 and H2, respectively) or having carboxyl group added to the 5- or 6-position of the nicotine pyridine ring (H3 and H4, respectively) are synthesized (Medchem Source, Federal Way, Wash.) (see FIG. 13). Linkers L1-L4 having a methyl ester (L1, L2) or tert-butyl (L3, L4) terminal group are also synthesized (see FIG. 13).

Nicotine Hapten-Linker Compounds:

Nicotine haptens H1 and H2 are conjugated to linkers L1 and L2 to yield structures 1 (H1-L1), 2 (H1-L2), 3 (H2-L1), 4 (H2-L2). Nicotine haptens H3 and H4 are conjugated to linkers L3 and L4 to yield structures 5 (H3-L4), 6 (H3-L3), 7 (H4-L4), and 8 (H4-L3).

Vaccines:

Peptide monomers having an amino acid sequence of SEQ ID NO: 13 (amphipathic α-helical peptide/PADRE epitope/CD4+ T cell hemagglutinin peptide) are self-assembled into TCC and nicotine hapten-linker compounds 1-8 (see FIG. 13) are conjugated to the TCC using EDC/NHS chemistry as previously described for maximal hapten loading. Haptens are also conjugated to control carriers, including for example, KLH, BSA, OVA, or polyglutamate.

Immunizations:

C57BL/6 mice (n=10/group) are immunized by intramuscular injection with 1 μg of each test vaccine with and without GLA-SE adjuvant on days 0, 14, and 146. PBS is used as a negative control, and TCC conjugated to nicotine hexanoic acid as previously described is used as a positive control. Sera are collected on days 21 and 42 for measuring anti-hapten, anti-carrier, and anti-linker antibody titers. Each sample is assayed in triplicate along with standard control sera. Mean midpoint and endpoint antibody titers (+/−SEM) are determined.

Antibody Affinity, Serum Binding Capacity, and Antibody Specificity:

Relative $K_d$ values of serum IgG are measured by soluble competitive RIA (with $H^3$-Nicotine as the tracer and non-radiolabeled nicotine as the inhibitor). Antiserum dilutions are adjusted so that only 40-70% of the tracer binds in the absence of inhibitor. Diluted antisera aliquots are incubated with equal concentrations of $^3$H-nicotine and varying concentrations of unlabeled nicotine (0.01-100 nM). Following equilibrium, IgG antibodies are precipitated by ammonium sulfate and the amount of tracer in the supernatant is measured by liquid scintillation spectrometry. Antibody affinity constants and binding capacity are calculated as previously described (see, e.g., Friguet et al., 1985, J. Immunol. Methods 77:305-19; Seligman, 1994, J. Immunol. Methods 168:101-10; Stevens, 1987, Mol. Immunol. 24:1055-60; Moreno et al., 2010, Mol. Pharm. 7:431-41). IgG specificity is determined by conveniently performing the same assays using cotinine, acetylcholine, linkers, etc. as inhibitors instead of nicotine.

In Vivo Functional Analysis:

Nicotine distribution in brain and plasma is determined on day 196 following infusion of 0.05 mg/kg of nicotine hydrogen tartrate in anesthetized animals. This nicotine dose is equivalent to approximately three smoked cigarettes (see, e.g., Matta, et al., *Psychopharmacology* (Berl), 2007. 190 (3): p. 269-31). Blood is collected 5 min later and plasma collected. Following exsanguinations, animals are perfused with PBS and the brain harvested, weighed, sectioned, and then frozen. Plasma and tissue samples are prepared, and nicotine is extracted and then quantified by LC/MS. The amounts of nicotine in plasma (ng/ml) and brain (ng/g) are determined, and the proportion of nicotine sequestered specifically in the blood provides a measure of efficacy.

Statistical Analysis:

Data are analyzed using GraphPad Prism (San Diego, Calif.). Statistically significant differences between 2 groups is calculated by Student's 2-tailed t-test on log transformed data and between 3 or more groups by 1-factor analysis of variance (ANOVA) followed by post-hoc analysis. Differences are considered significant with p<0.05.

Four nicotine haptens (synthesized by Medchem Source, Federal Way, Wash.) containing attachment sites on the 5- or 6-position of the nicotine pyridine ring in combination with four different linkers with varying lengths that introduce subtle changes in electronegativity and conformation (see FIG. 13). Without wishing to be bound by theory, these changes in electronegativity and conformation may influence antigen presentation and B cell activation.

Sequence Table:

| SEQ ID NO: # | Amino Acid Sequence |
|---|---|
| 1 | KKIEKRIEKIEKRIKKIEKRIKKIEKRIKKIEKRIKK |
| 2 | KKIEKRIEKIEKRIKKIEKRIKKIEKRIKKIEKRIKK IEKRIEKIEKRIKKIEKRIEKIEKRIKK |
| 3 | DDIEDRIEDIEDRIDDIEDRIDDIEDRIDDIEDRIDD |
| 4 | (E or X)XIEXR-[I(E or X)XIEXR]$_n$-I |
| 5 | (E or X)X; where X = K for each instance, or each X is independently selected from E or D, and n = 1-20; i.e., represented by (E or K)KIEKR-[I(E or K)KIEKR]$_n$-I(E or K)K [SEQ ID NO: 4] and (E or D)(E or D)IE(E or D)R-[I(E or D)(E or D)IE(E or D)R]$_n$-I(E or D)(E or D) [SEQ ID NO: 5] |
| 6 | YQNPTTYISVK |
| 7 | SLEHPIVVSGSWD |
| 8 | ILMQYIKANSKFIGI |
| 9 | QSIALSSLMVAQ |

Sequence Table:

| SEQ ID NO: # | Amino Acid Sequence |
|---|---|
| 10 | AKFVAAWTLKAAA |
| 11 | PMGLP |
| 12 | KVSVR |
| 13 | KKIEKRIEKIEKRIKKIEKRIKKI EKRIKKIEKRIKKAKFVAAWTLKAAAYQNPTTYISVK |
| 14 | KKI EKR IEK IEK RIK KIE KRI KKI EKR IKK IEK RIK KSL EHP IVV SGS WD |
| 15 | KKI EKR IEK IEK RIK KIE KRI KKI EKR IKK IEK RIK KIE KRI EKI EKR IKK IEK RIE KIE KRI KKS LEH PIV VSG SWD |

The various embodiments described above can be combined to provide further embodiments. All U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A peptide monomer comprising an amphipathic α-helical peptide comprising an amino acid sequence with at least 80% identity to SEQ ID NO:1, SEQ ID NO:2, or SEQ ID NO:3.

2. The peptide monomer of claim 1, wherein the amphipathic α-helical peptide comprises an amino acid sequence with at least 90% identity to SEQ ID NO:1, SEQ ID NO:2, or SEQ ID NO:3.

3. The peptide monomer of claim 1, wherein the amphipathic α-helical peptide comprises an amino acid sequence with 100% identity to SEQ ID NO:1, SEQ ID NO:2, or SEQ ID NO:3.

4. The peptide monomer of claim 1, further comprising at least one T cell epitope peptide linked to the C-terminus of the amphipathic α-helical peptide.

5. The peptide monomer according to claim 1, wherein the amphipathic α-helical peptide comprises an amino acid sequence according to the formula: (E or X)XIEXR-[I(E or X)XIEXR]$_n$-I(E or X)X,
wherein X=K for each instance; or each X is independently selected from D and E; and n=3, 4, 5, 6, 7, 8, 9, or 10.

6. The peptide monomer according to claim 4, wherein the amphipathic α-helical peptide comprises an amino acid sequence according to the formula: (E or X)XIEXR-[I(E or X)XIEXR]$_n$-I(E or X)X,
wherein X=K for each instance; or each X is independently selected from D and E; and n=3, 4, 5, 6, 7, 8, 9, or 10.

7. The peptide monomer according to claim 4, wherein the at least one T cell epitope peptide is a CD4$^+$ T cell epitope peptide.

8. The peptide monomer of claim 4, wherein the CD4$^+$ T cell epitope peptide is a promiscuous CD4$^+$ T cell epitope peptide or comprises the amino acid sequence set forth in SEQ ID NO:10.

9. The peptide monomer of claim 4, wherein the at least one T cell epitope peptide is a T cell epitope peptide of a pathogenic microorganism or is an influenza hemagglutinin T cell epitope peptide.

10. The peptide monomer of claim 9, wherein the at least one T cell epitope peptide comprises the amino acid sequence set forth in SEQ ID NO:6.

11. The peptide monomer of claim 4, wherein at least two T cell epitope peptides are fused in series to the C-terminus of the amphipathic α-helical peptide.

12. A peptide dimer comprising a peptide monomer according to claim 1, wherein the peptide dimer is configured in a coiled-coil, comprising a parallel bundle of the two peptide monomers.

13. A peptide dimer comprising a peptide monomer according to claim 4, wherein the peptide dimer is configured in a coiled-coil, comprising a parallel bundle of the two peptide monomers.

14. A trimeric peptide comprising a peptide monomer according to claim 1, wherein the trimeric peptide is configured in a coiled-coil, comprising a parallel bundle of the three peptide monomers.

15. A trimeric peptide comprising a peptide monomer according to claim 4, wherein the trimeric peptide is configured in a coiled-coil, comprising a parallel bundle of the three peptide monomers.

16. A peptide carrier conjugate comprising the trimeric coiled-coil peptide of claim 14 linked to at least one hapten, wherein the at least one hapten is linked to a lysine or aspartic acid or glutamic acid residue of at least one peptide monomer of said three peptide monomers of which the trimeric coiled-coil peptide is comprised.

17. A peptide carrier conjugate comprising the trimeric coiled-coil peptide of claim 15 linked to at least one hapten, wherein the at least one hapten is linked to a lysine or aspartic acid or glutamic acid residue of at least one peptide monomer of said three peptide monomers of which the trimeric coiled-coil peptide is comprised.

18. The peptide carrier conjugate of claim 16, wherein the hapten is a drug of abuse.

19. The peptide carrier conjugate of claim 17, wherein the hapten is a drug of abuse.

20. The peptide carrier conjugate of claim 18, wherein the drug of abuse is nicotine, cocaine, methamphetamine, morphine, a cannabinoid, or an analog thereof.

21. The peptide carrier conjugate of claim 19, wherein the drug of abuse is nicotine, cocaine, methamphetamine, morphine, a cannabinoid, or an analog thereof.

22. The peptide carrier conjugate of claim 20, wherein the nicotine analog is nicotine 6-hexanoic acid.

23. The peptide carrier conjugate of claim 21, wherein the nicotine analog is nicotine 6-hexanoic acid.

24. The peptide carrier conjugate of claim 16, wherein the peptide carrier conjugate is linked to at least two haptens.

25. The peptide carrier conjugate of claim 17, wherein the peptide carrier conjugate is linked to at least two haptens.

26. The peptide carrier conjugate of claim 24, wherein the at least two haptens are selected from nicotine, nicotine analogs, and structurally distinct nicotine haptens.

27. The peptide carrier conjugate of claim 25, wherein the at least two haptens are selected from nicotine, nicotine analogs, and structurally distinct nicotine haptens.

28. An immunogenic composition comprising the peptide carrier conjugate of claim 16; and a pharmaceutically acceptable carrier, wherein the composition is capable of inducing an immune response specific for the hapten.

29. An immunogenic composition comprising the peptide carrier conjugate of claim 17; and a pharmaceutically acceptable carrier, wherein the composition is capable of inducing an immune response specific for the hapten.

30. The immunogenic composition of claim 28, wherein the immunogenic composition further comprises at least one T cell epitope peptide.

31. The immunogenic composition according to claim 28, further comprising a pharmaceutically acceptable adjuvant.

32. The immunogenic composition according to claim 29, further comprising a pharmaceutically acceptable adjuvant.

33. The immunogenic composition of claim 31, wherein the adjuvant is a toll-like receptor (TLR) agonist.

34. The immunogenic composition of claim 32, wherein the adjuvant is a toll-like receptor (TLR) agonist.

35. A method of inducing an immune response specific for a hapten in a subject, the method comprising administering to the subject the immunogenic composition according to claim 28.

36. A method of inducing an immune response specific for a hapten in a subject, the method comprising administering to the subject the immunogenic composition according to claim 29.

* * * * *

SEQUENCE LISTING

```
<160> NUMBER OF SEQ ID NOS: 18

<210> SEQ ID NO 1
<211> LENGTH: 37
<212> TYPE: PRT
<213> ORGANISM: Artificial Sequence
<220> FEATURE:
<223> OTHER INFORMATION: Synthetic peptide

<400> SEQUENCE: 1

Lys Lys Ile Glu Lys Arg Ile Glu Lys Ile Glu Lys Arg Ile Lys Lys
1               5                   10                  15

Ile Glu Lys Arg Ile Lys Lys Ile Glu Lys Arg Ile Lys Lys Ile Glu
                20                  25                  30

Lys Arg Ile Lys Lys
            35

<210> SEQ ID NO 2
<211> LENGTH: 65
<212> TYPE: PRT
<213> ORGANISM: Artificial Sequence
<220> FEATURE:
<223> OTHER INFORMATION: Synthetic peptide
```

```
<400> SEQUENCE: 2

Lys Lys Ile Glu Lys Arg Ile Glu Ile Glu Lys Arg Ile Lys Lys
1               5                   10                  15

Ile Glu Lys Arg Ile Lys Lys Ile Glu Lys Arg Ile Lys Lys Ile Glu
                20                  25                  30

Lys Arg Ile Lys Lys Ile Glu Lys Arg Ile Glu Ile Glu Lys Arg
        35                  40                  45

Ile Lys Lys Ile Glu Lys Arg Ile Glu Lys Ile Glu Lys Arg Ile Lys
        50                  55                  60

Lys
65

<210> SEQ ID NO 3
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 3

Asp Asp Ile Glu Asp Arg Ile Glu Ile Glu Asp Arg Ile Asp Asp
1               5                   10                  15

Ile Glu Asp Arg Ile Asp Asp Ile Glu Asp Arg Ile Asp Asp Ile Glu
                20                  25                  30

Asp Arg Ile Asp Asp
        35

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: 1
<223> OTHER INFORMATION: Glutamic Acid or Lysine
<220> FEATURE:
<221> NAME/KEY: PEPTIDE
<222> LOCATION: 8
<223> OTHER INFORMATION: Glutamic Acid or Lysine
<220> FEATURE:
<221> NAME/KEY: REPEAT
<222> LOCATION: (7)...(13)
<223> OTHER INFORMATION: n=1-20
<220> FEATURE:
<221> NAME/KEY: PEPTIDE
<222> LOCATION: 15
<223> OTHER INFORMATION: Glutamic Acid or Lysine

<400> SEQUENCE: 4

Xaa Lys Ile Glu Lys Arg Ile Xaa Lys Ile Glu Lys Arg Ile Xaa Lys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: 1
<223> OTHER INFORMATION: Glutamic Acid or Aspartic Acid
```

```
<220> FEATURE:
<221> NAME/KEY: PEPTIDE
<222> LOCATION: 2
<223> OTHER INFORMATION: Glutamic Acid or Aspartic Acid
<220> FEATURE:
<221> NAME/KEY: PEPTIDE
<222> LOCATION: 5
<223> OTHER INFORMATION: Glutamic Acid or Aspartic Acid
<220> FEATURE:
<221> NAME/KEY: PEPTIDE
<222> LOCATION: 8
<223> OTHER INFORMATION: Glutamic Acid or Aspartic Acid
<220> FEATURE:
<221> NAME/KEY: PEPTIDE
<222> LOCATION: 9
<223> OTHER INFORMATION: Glutamic Acid or Aspartic Acid
<220> FEATURE:
<221> NAME/KEY: PEPTIDE
<222> LOCATION: (12)...(12)
<223> OTHER INFORMATION: Glutamic Acid or Aspartic Acid
<220> FEATURE:
<221> NAME/KEY: REPEAT
<222> LOCATION: (7)...(13)
<223> OTHER INFORMATION: n=1-20
<220> FEATURE:
<221> NAME/KEY: PEPTIDE
<222> LOCATION: (15)...(15)
<223> OTHER INFORMATION: Glutamic Acid or Aspartic Acid
<220> FEATURE:
<221> NAME/KEY: PEPTIDE
<222> LOCATION: (16)...(16)
<223> OTHER INFORMATION: Glutamic Acid or Aspartic Acid

<400> SEQUENCE: 5

Xaa Xaa Ile Glu Xaa Arg Ile Xaa Xaa Ile Glu Xaa Arg Ile Xaa Xaa
 1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Tyr Gln Asn Pro Thr Thr Tyr Ile Ser Val Lys
 1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 7

Ser Leu Glu His Pro Ile Val Val Ser Gly Ser Trp Asp
 1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Ile Leu Met Gln Tyr Ile Lys Ala Asn Ser Lys Phe Ile Gly Ile
 1               5                   10                  15
```

```
<210> SEQ ID NO 9
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 9

Gln Ser Ile Ala Leu Ser Ser Leu Met Val Ala Gln
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 10

Ala Lys Phe Val Ala Ala Trp Thr Leu Lys Ala Ala Ala
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Pro Met Gly Leu Pro
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 12

Lys Val Ser Val Arg
1               5

<210> SEQ ID NO 13
<211> LENGTH: 61
<212> TYPE: PRT
<213> ORGANISM: Artificial Sequence
<220> FEATURE:
<223> OTHER INFORMATION: Synthetic Peptide

<400> SEQUENCE: 13

Lys Lys Ile Glu Lys Arg Ile Glu Lys Ile Glu Lys Arg Ile Lys Lys
1               5                   10                  15

Ile Glu Lys Arg Ile Lys Lys Ile Glu Lys Arg Ile Lys Lys Ile Glu
                20                  25                  30

Lys Arg Ile Lys Lys Ala Lys Phe Val Ala Ala Trp Thr Leu Lys Ala
            35                  40                  45

Ala Ala Tyr Gln Asn Pro Thr Thr Tyr Ile Ser Val Lys
        50                  55                  60

<210> SEQ ID NO 14
<211> LENGTH: 50
<212> TYPE: PRT
<213> ORGANISM: Artificial Sequence
```

```
<220> FEATURE:
<223> OTHER INFORMATION: Synthetic Peptide

<400> SEQUENCE: 14

Lys Lys Ile Glu Lys Arg Ile Glu Lys Ile Glu Lys Arg Ile Lys Lys
1               5                   10                  15

Ile Glu Lys Arg Ile Lys Lys Ile Glu Lys Arg Ile Lys Lys Ile Glu
            20                  25                  30

Lys Arg Ile Lys Lys Ser Leu Glu His Pro Ile Val Val Ser Gly Ser
        35                  40                  45

Trp Asp
    50

<210> SEQ ID NO 15
<211> LENGTH: 78
<212> TYPE: PRT
<213> ORGANISM: Artificial Sequence
<220> FEATURE:
<223> OTHER INFORMATION: Synthetic Peptide

<400> SEQUENCE: 15

Lys Lys Ile Glu Lys Arg Ile Glu Lys Ile Glu Lys Arg Ile Lys Lys
1               5                   10                  15

Ile Glu Lys Arg Ile Lys Lys Ile Glu Lys Arg Ile Lys Lys Ile Glu
            20                  25                  30

Lys Arg Ile Lys Lys Ile Glu Lys Arg Ile Glu Lys Ile Glu Lys Arg
        35                  40                  45

Ile Lys Lys Ile Glu Lys Arg Ile Glu Lys Ile Glu Lys Arg Ile Lys
    50                  55                  60

Lys Ser Leu Glu His Pro Ile Val Val Ser Gly Ser Trp Asp
65                  70                  75

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = Glu or Asp

<400> SEQUENCE: 16

Ile Xaa Asp Ile Glu Asp Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 2
<223> OTHER INFORMATION: Xaa = Glu or Lys

<400> SEQUENCE: 17

Ile Xaa Lys Ile Glu Lys Arg
1               5
```

```
<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Ile Glu Glu Ile Glu Glu Arg
 1               5
```